US006350739B1

(12) United States Patent
Simpkins et al.

(10) Patent No.: US 6,350,739 B1
(45) Date of Patent: Feb. 26, 2002

(54) METHODS OF PREVENTION AND TREATMENT OF ISCHEMIC DAMAGE

(75) Inventors: James W. Simpkins, Gainesville, FL (US); Douglas F. Covey, Ballwin, MO (US)

(73) Assignees: University of Florida Resarch Foundation, Inc., Gainesville, FL (US); Washington University, St. Louis, MO (US)

( * ) Notice: Subject to any disclaimer, the term of this patent is extended or adjusted under 35 U.S.C. 154(b) by 0 days.

(21) Appl. No.: 09/372,627

(22) Filed: Aug. 11, 1999

(51) Int. Cl.[7] .............................................. A61K 31/56
(52) U.S. Cl. ...................... 514/182; 514/179; 514/180; 514/181
(58) Field of Search ................................ 514/179, 180, 514/181, 182

(56) References Cited

U.S. PATENT DOCUMENTS

| | | | |
|---|---|---|---|
| 5,550,029 A | | 8/1996 | Simpkins et al. .............. 435/14 |
| 5,554,601 A | * | 9/1996 | Simpkins et al. ............ 514/182 |
| 5,824,672 A | | 10/1998 | Simpkins et al. ............ 514/182 |
| 5,843,934 A | * | 12/1998 | Simpkins et al. ............ 514/182 |
| 5,859,001 A | | 1/1999 | Simpkins et al. ............ 514/182 |
| 5,877,169 A | * | 3/1999 | Simpkins ..................... 514/179 |
| 5,972,923 A | | 10/1999 | Simpkins et al. ............ 514/182 |

FOREIGN PATENT DOCUMENTS

| | | | |
|---|---|---|---|
| WO | WO 95/13076 | 5/1995 | |
| WO | WO 00/63228 | 10/2000 | ............ C07J/15/00 |

OTHER PUBLICATIONS

Arvidson, N., et al., Oestrogens and anti–oestrogens show dissoaciation between early uterine vasular responses an uterophic effects in mice, Acta Endocrinolgica 1982, 100:290–294.

Buzby, Jr., G.C., et al. Totally Synthetic Steroid Hormones. XIII. The Chemical Resolution of Some Raccmic Estrane , 13β–Ethygonane, and 13 β–n–Proplygonane Derivatives and the Preparation of Some Estrane and 13β–*Ethylgonane Derivatives of Unnatural Configuration*, J. Med. Chem. (1967) 10(2): 199–204.

Chernyaev, G.A., et al., A Series of Optical, Structural and Isomeric Analogs of Estradiol: A Comparative Study of the Biological Activity and Affinity to Cytosol Receptor of Rabbit Uterusl , The Journal of Steroid Biochemistry, vol. 6, pp 1483–1488, 1975.

Edgren, R.A., et al., An Anti–Estradiol Effect of ENT Estradiol –1β (1–Estradiol), Steroids, vol. 14, No. 3, pp. 335–341, 1969.

Green, P.S., et al., *Ent–Estradiol Exerts Neuroprotective Effects in Vitro and In Vivo*, Society for Neuroscience 1999 Abstract Form, 1999 Annual Meeting, Miami Beach, Florida, USA, Oct. 23–28, 1999.

Pons, M., et al., Structural Requirements for Maximal Inhibitory Allosteric Effect of Estrogens and Estrogen Analogues on Glutamate Dehydrogenase , Eur. J. Biochemistry, vol. 84, pp. 257–266, 1978.

Resnik, R., et al., The Simulation of Uterine Blood Flow by Various Estrogens , Endocrinology, vol. 94, No .4, pp. 1192–1196.

Terenius, Lars, Differential Inhibition in Vitro of 17β–Estradiol Binding in the Mouse Uterus and Vagina by Optical Atipodes of Estrogens, Molecular Pharmacology, vol. 4, pp. 301–310, 1968.

Terenius, Lars, Structure–Activity Relationships of Anti–I–estrogens with Regard to Interactio with 17β–*Oestradiol in the Mouse Uterus and Vagina*, Acta Endocrinology (1971) 66(3): pp 431–437.

Terenius, Lars, The Allen–Doisy Test for Estrogens Reinvestigatedl , Steroids, vol. 17, No. 6, pp. 653–661, 1971.

Kim et al., 17 beta–estradiol prevents dysfunction of canine coronary endothelium and myocardium and reperfusion arrhythmic after brief ischemia/repertusion., Circulation, 94(11), pp. 2901–2908, (1986) see abs.*

* cited by examiner

*Primary Examiner*—Kevin E. Weddington
(74) *Attorney, Agent, or Firm*—Bromberg & Sunstein LLP

(57) ABSTRACT

The present invention in various embodiments provides methods of treating stroke and conferring protection on a population of cells associated with ischemia in a subject following an ischemic event, comprising: (a) providing an estrogen compound; and (b) administering the effective amount of the compound over a course that includes at least one dose within a time that is effectively proximate to the ischemic event, so as to confer protection on the population of cells. Novel methods are provided for the delivery of an estrogen compound. Examples of ischemic events treatable according to the invention are cerebrovascular disease or stroke, subarachnoid subhemorrhage, myocardial infarct, surgery and trauma. A method of treating ischemic damage utilizing hormones that are non-sex hormones is also provided. A method of treating stroke with ent-17β-estradiol, and a method of synthesis, and compounds produced from the synthesis are provided.

22 Claims, 10 Drawing Sheets

METHODS OF PREVENTION AND TREATMENT OF ISCHEMIC DAMAGE

GOVERNMENT SUPPORT

This invention herein was made in part with government support under grant GM47967 from the NIH. The government has certain rights in the invention.

TECHNICAL FIELD

The present invention relates to the protection of cells that would otherwise die as a result of stroke or an ischemic event.

BACKGROUND

Ischemia is an acute condition associated with an inadequate flow of oxygenated blood to a part of the body, caused by the constriction or blockage of the blood vessels supplying it. Ischemia occurs any time that blood flow to a tissue is reduced below a critical level. This reduction in blood flow can result from: (i) the blockage of a vessel by an embolus (blood clot); (ii) the blockage of a vessel due to atherosclerosis; (iii) the breakage of a blood vessel (a bleeding stroke); (iv) the blockage of a blood vessel due to vasoconstriction such as occurs during vasospasms and possibly, during transient ischemic attacks (TIA) and following subarachnoid hemorrhage. Conditions in which ischemia occurs further include (i) myocardial infarction; (ii) trauma; and (iii) during cardiac and thoracic surgery and neurosurgery (blood flow needs to be reduced or stopped to achieve the aims of surgery). During myocardial infarct, stoppage of the heart or damage occurs which reduces the flow of blood to organs, and ischemia results. Cardiac tissue itself is also subjected to ischemic damage. During various surgeries, reduction of blood flow, clots or air bubbles generated can lead to significant ischemic damage.

When an ischemic event occurs, there is a gradation of injury that arises from the ischemic site. The cells at the site of blood flow restriction, undergo necrosis and form the core of a lesion. A penumbra is formed around the core where the injury is not immediately fatal but progresses slowly toward cell death. This progression to cell death may be reversed upon reestablishment of blood flow within a short time of the ischemic event.

Focal ischemia encompasses cerebrovascular disease (stroke), subarachnoid hemorrhage (SAH) and trauma Stroke is the third leading cause of morbidity in the United States, with over 500,000 cases per year, including 150,000 deaths annually. Post-stroke sequelae are mortality and debilitating chronic neurological complications which result from neuronal damage for which prevention or treatment are not currently available.

Following a stroke, the core area shows signs of cell death, but cells in the penumbra remain alive for a period of time although malfunctioning and will, in several days, resemble the necrotic core. The neurons in the penumbra seem to malfunction in a graded manner with respect to regional blood flow. As the blood flow is depleted, neurons fall electrically silent, their ionic gradients decay, the cells depolarize and then they die. Endothelial cells of the brain capillaries undergo swelling and the luminal diameter of the capillaries decrease. Associated with these events, the blood brain barrier appears to be disrupted, and an inflammatory response follows which further interrupts blood flow and the access of cells to oxygen.

The effects of a stroke on neurons result from the depletion of energy sources associated with oxygen deprivation which in turn disrupts the critically important ion pumps responsible for electrical signaling and neurotransmitter release. The failure of the ATP-dependant ion specific pumps to maintain ion gradients through active transport of sodium, chlorine, hydrogen, and calcium ions out of the cell and potassium ions into the cell results in a series of adverse biochemical events. For example, increase in intracellular calcium ion levels results in: (I) the production of free radicals that extensively damage lipids and proteins; (ii) the disruption of calcium sensitive receptors such as the N-methyl D-aspartate (NMDA) and the α-amino-3-hydroxy-5-methyl-4-isoxazolepropionic acid (AMPA) synaptic glutamate receptors; (iii) the swelling of cells with water as a result of abnormal accumulation of ions; and (iv) the decrease in intracellular pH. The alteration in metabolism within the cell further results in the accumulation of ions in the cells as energy sources are depleted. For example, anaerobic glycolysis that forms lactic acid, replaces the normal aerobic glycolysis pathways in the mitochondria. This results in acidosis that results in further accumulation of calcium ions in the cell.

Despite the frequency of occurrence of ischemia (including stroke) and despite the serious nature of the outcome for the patient, treatments for these conditions have proven to be elusive. There are two basic approaches that have been undertaken to rescue degenerating cells in the penumbra. The first and most effective approach to date has been the identification of blood clot dissolvers that bring about rapid removal of the vascular blockage that restricts blood flow to the cells. Recombinant tissue plasminogen activator (TPA) has been approved by the Federal Drug Administration for use in dissolving clots that cause ischemia in thrombotic stroke. Nevertheless, adverse side effects are associated with the use of TPA. For example, a consequence of the breakdown of blood clots by TPA treatment is cerebral hemorrhaging that results from blood vessel damage caused by the ischemia. A second basic approach to treating degenerating cells deprived of oxygen is to protect the cells from damage that accumulates from the associated energy deficit. To this end, glutamate antagonists and calcium channel antagonists have been most thoroughly investigated. None of these have proven to be substantially efficacious but they are still in early clinical development. The pathophysiology and treatment of focal cerebral ischemia has been reviewed by B. K. Seisjo, J. Neurosurgery, 1992, vol. 77, p. 169–184 and 337–354.

In addition to the targets of drug development described by Seisjo (1992), epidemiological studies have shown that women undergoing hormone replacement therapy with estrogen and progesterone experienced a reduction in the incidence and severity of heart disease. This correlation was further investigated for stroke with mixed results. A 10-year epidemiological study on 48,000 women reported by Stampfer et al. (New England Journal of Medicine, 1991, vol. 325, p. 756) concluded that there was a correlation between use of estrogen and decrease in incidence of coronary heart disease, but no decrease in the incidence of stroke was observed. In contrast, a report by Wren (The Medical Journal of Australia, 1992, vol. 157, p. 204) who reviewed 100 articles directed to the question as to whether estrogens reduce the risk of atherosclerosis and myocardial infarction, concluded that estrogens in hormone replacement therapies significantly reduce the incidence of myocardial infarction and stroke and may accomplish this at the site of the blood vessel wall. This conclusion was further supported by Falkeborn et al. Arch Intern. Med., 1993, vol. 153, p. 1201. The above correlation between estrogen replacement therapy and reduced incidence of stroke relies on epidemiological data only. No biochemical data were analyzed to interpret or support these conclusions, nor is there any information as to reduction in ischemic lesion or morbidity with hormone use. Furthermore, these studies were restricted to the patients receiving long-term hormone replacement treatment. No studies were performed on patients who might be administered estrogen therapeutically shortly before, during, or after a stroke for the first time. Furthermore, the studies were limited to estrogens utilized in estrogen replacement therapy. No studies were performed on any non-sex related estrogens that might be used in treating males or females.

Studies have been conducted on the neuroprotective effects of steroids in which glucocorticosteroid for example was found to have a positive effect in reducing spinal cord injury but had a negative effect on hippocampal neurodegeneration. For example, Hall (J. Neurosurg vol. 76, 13–22 (1992)) noted that the glucocorticoid steroid, methylprednisolone, believed to involve the inhibition of oxygen free radical-induced lipid peroxidation, could improve the 6-month recovery of patients with spinal cord injury when administered in an intensive 24hour intravenous regimen beginning within 8 hours after injury. However, when the steroid was examined for selective protection of neuronal necrosis of hippocampal neurons, it was found that the hippocampal neuronal loss was significantly worsened by glucocorticoid steroid dosing suggesting that this hormone is unsuitable for treating acute cerebral ischemic. Hall reported that substitution of a complex amine on a non-glucocorticoid steroid in place of the 21'-hydroxyl functionality results in an enhancement of lipid anti-oxidant activity. No data were provided concerning the behavior of this molecule in treating ischemic events or in neuroprotection of neurons in the brain. Additionally, free radical scavenging activity has been reported for a lazaroid, another non-glucocorticoid steroid having a substituted 21'-hydroxyl functionality, but there is no evidence that this compound is significantly efficacious for treating stroke or other forms of ischemia.

SUMMARY

The invention satisfies the above need. Novel methods are provided for prevention and treatment of ischemic damage using estrogen compounds.

A preferred embodiment of the invention provides a method for conferring protection on a population of cells associated with an ischemic focus, in a subject following an ischemic event that includes the steps of providing subcutaneously an estrogen compound in a drug delivery system in which the estrogen compound is dissolved in oil with or without additional excipients such as solvents, stabilizers or preservatives, so as to confer protection on the population of cells. Further embodiments include selecting a proximate time for administering the effective dose of the estrogen compound that is prior to the ischemic event. Alternatively, the estrogen compound may be administered within an effective proximate time after the ischemic event. The method of the invention may be applied to any of a cerebrovascular disease, subarachnoid hemorrhage, myocardial infarct, surgery, and trauma. In particular, when the ischemic event is a stroke, the protected cells include at least one of neurons and endothelial cells.

The method utilizes an estrogen compound that may include alpha isomers or beta isomers of estrogen compounds. Examples of different isomers are provided wherein the estrogen compound is selected from the group consisting of 17α-estradiol and 17β-estradiol.

In a preferred embodiment of the invention, a method is provided for protecting cells in a subject from degeneration during or after an ischemic event. The steps of the method include identifying a susceptible subject, providing an effective dose of an estrogen compound prior to or after the ischemic event, and protecting cells from degeneration otherwise occurring in the absence of the estrogen compound.

In a further embodiment of the invention, a method is provided for treating stroke in a subject, including the steps of providing an effective dose of an estrogen compound in a pharmaceutical formulation and administering the formulation to the subject so as to reduce the adverse effects of the stroke.

The invention in another embodiment provides a method for conferring protection on a population of cells associated with ischemia, in a subject following an ischemic event, comprising: (a) providing an estrogen compound formulated in an oil vehicle; and (b) administering an effective amount of the compound over a course that includes at least one dose within a time that is effectively proximate to the ischemic event, so as to confer protection on the population of cells. Further in this embodiment in (b) the estrogen compound is administered by subcutaneous injection.

In another embodiment, the invention provides a method of synthesis of ent-17β-estradiol from [3R-(3α,3aα,9aα,9bβ)]-3-(1,1-dimethylethoxy)-1,2,3,3a,4,5,8,9,9a,9b-decahydro-3a-methyl-6-[2-(2-methyl-1,3-dioxolan-2-yl)ethyl-7H-benz[e]inden-7-one, comprising: reducing the double bond of [3R-(3α,3aα,9aα,9bβ)]-3-(1,1-dimethylethoxy)-1,2,3,3a,4,5,8,9,9a,9b-decahydro-3a-methyl-6-[2-(2-methyl-1,3-dioxolan-2-yl)ethyl-7H-benz[e]inden-7-one to obtain tricyclic compound [3R-(3α,3aα,5aβ,6β,9aα,9bβ)]-3-(1,1-dimethylethoxy)-dodecahydro-3a-methyl-6-[2-(2-methyl-1,3-dioxolan-2-yl)ethyl-7H-benz[e]inden-7-one; cyclizing the tricyclic compound [3R-(3α,3aα,5aβ,6β,9aα,9bβ)]-3-(1,1-dimethylethoxy)-dodecahydro-3a-methyl-6-[2-(2-methyl-1,3-dioxolan-2-yl)ethyl-7H-benz[e]inden-7-one to obtain ent-19-nortestosterone; esterifying the hydroxy group of ent-19-nortestosterone to obtain ent-19-nortestosterone,17-acetate; aromatizing the steroid A ring of ent-19-nortestosterone,17-acetate to obtain ent-17β-estradiol,17-acetate; and saponifying ent-17β-estradiol,17-acetate to remove the 17-acetate group, to obtain ent-17β-estradiol.

According to this method, reducing the double bond of [3R-(3α,3aα,9aα,9bβ)]-3-(1,1-dimethylethoxy)-1,2,3,3a,4,5,8,9,9a,9b-decahydro-3a-methyl-6-[2-(2-methyl-1,3-dioxolan-2-yl)ethyl-7H-benz[e]inden-7-one is obtained by a step selected from the group consisting of: using lithium in liquid ammonia, and using catalytic hydrogenation.

Another embodiment of the invention provides the compound [3R-(3α,3aα,5aβ,6β,9aα,9bβ)]-3-(1,1-dimethylethoxy)-dodecahydro-3a-methyl-6-[2-(2-methyl-1,3-dioxolan-2-yl)ethyl-7H-benz[e]inden-7-one.

A further embodiment of the invention provides the compound ent-17β-estradiol,17-acetate. Yet another embodiment of the invention is the compound ent-19-nortestosterone, 17-acetate.

BRIEF DESCRIPTION OF THE DRAWINGS

These and other features, aspects, and advantages of the present invention will be better understood with reference to the following description, appended claims, and accompanying drawings, where:

FIG. 1. is a bar graph that shows the effects of pretreatment of ovariectomized rats, with 17β-estradiol, initiated 24 hours prior to ischemia induced by middle cerebral artery occlusion (MCAO); where the 17β-estradiol is administered as a subcutaneous 5 mm Silastic® implant (E2) or via the estradiol-chemical delivery system (E2-CDS) (1 mg/kg body weight) and a control is provided (a sham pellet). Values are given as the mean plus and minus the standard error of the mean (±SEM) for the percent ischemic area in 3 brain slices. The asterisk indicates that the observed p value was less than 0.05 (*=p<0.05) vs. sham group, that is, that the difference between the data for the experimental group and the sham group was statistically significant The number of samples for sham=6, for 17β-estradiol=8, and for E2-CDS groups=10.

Figure 2:
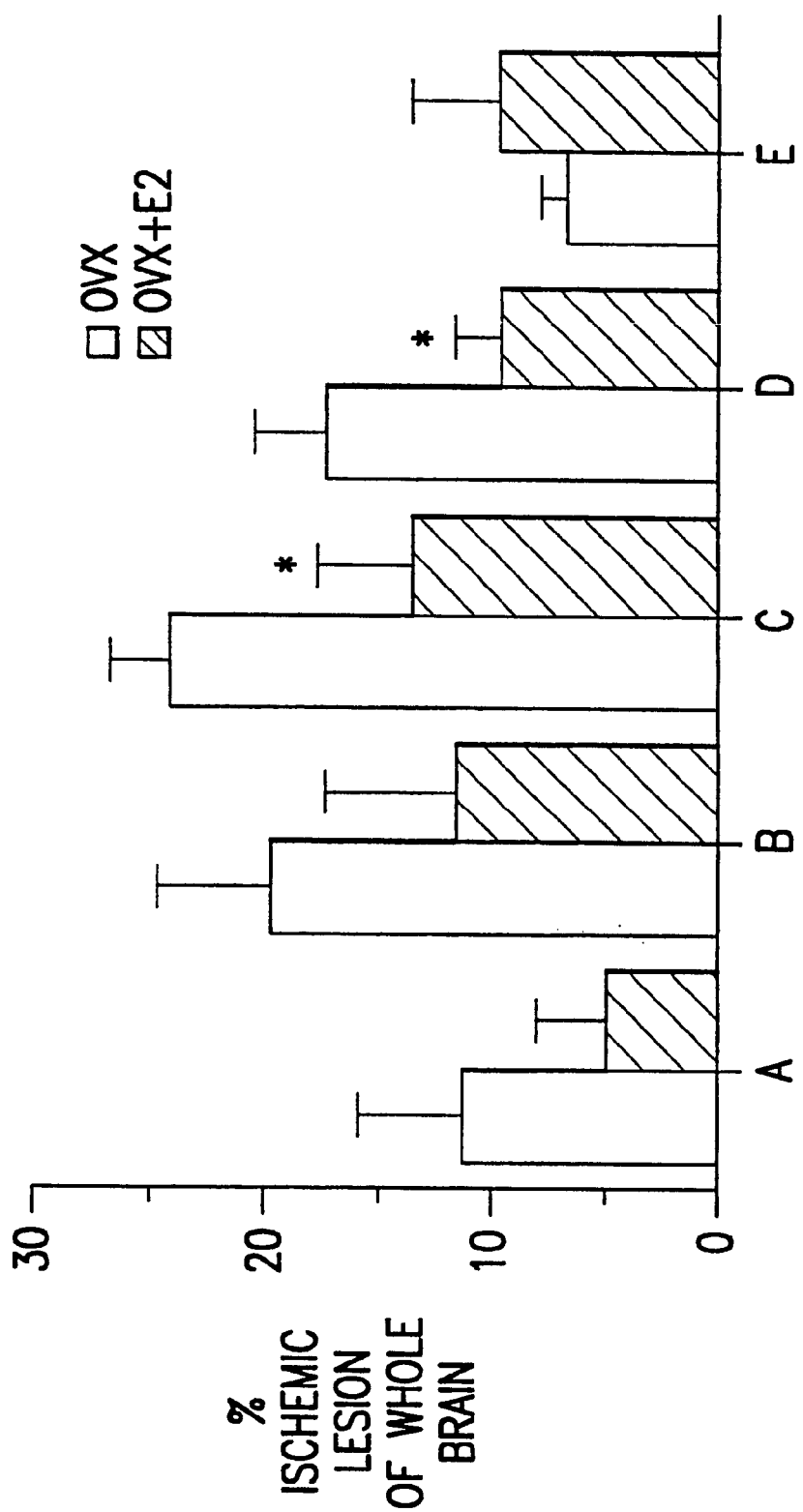

FIG. 2. is a bar graph that shows the effects of treatment of ovariectomized (OVX) rats with 17β-estradiol, at 2 hours prior to ischemia induced by MCAO, where the 17β-estradiol (10 μg/kg) is injected subcutaneously in an oil vehicle. Rats were decapitated 24 hours after the MCAO. Rat brains were dissected coronally as region A-E, 24 hours after MCAO. Values were given as the mean ±SEM where n=8 for OVX+E2 group and n=6 for OVX group(control). * p<0.05 vs. corresponding vehicle control groups.

Figure 3:
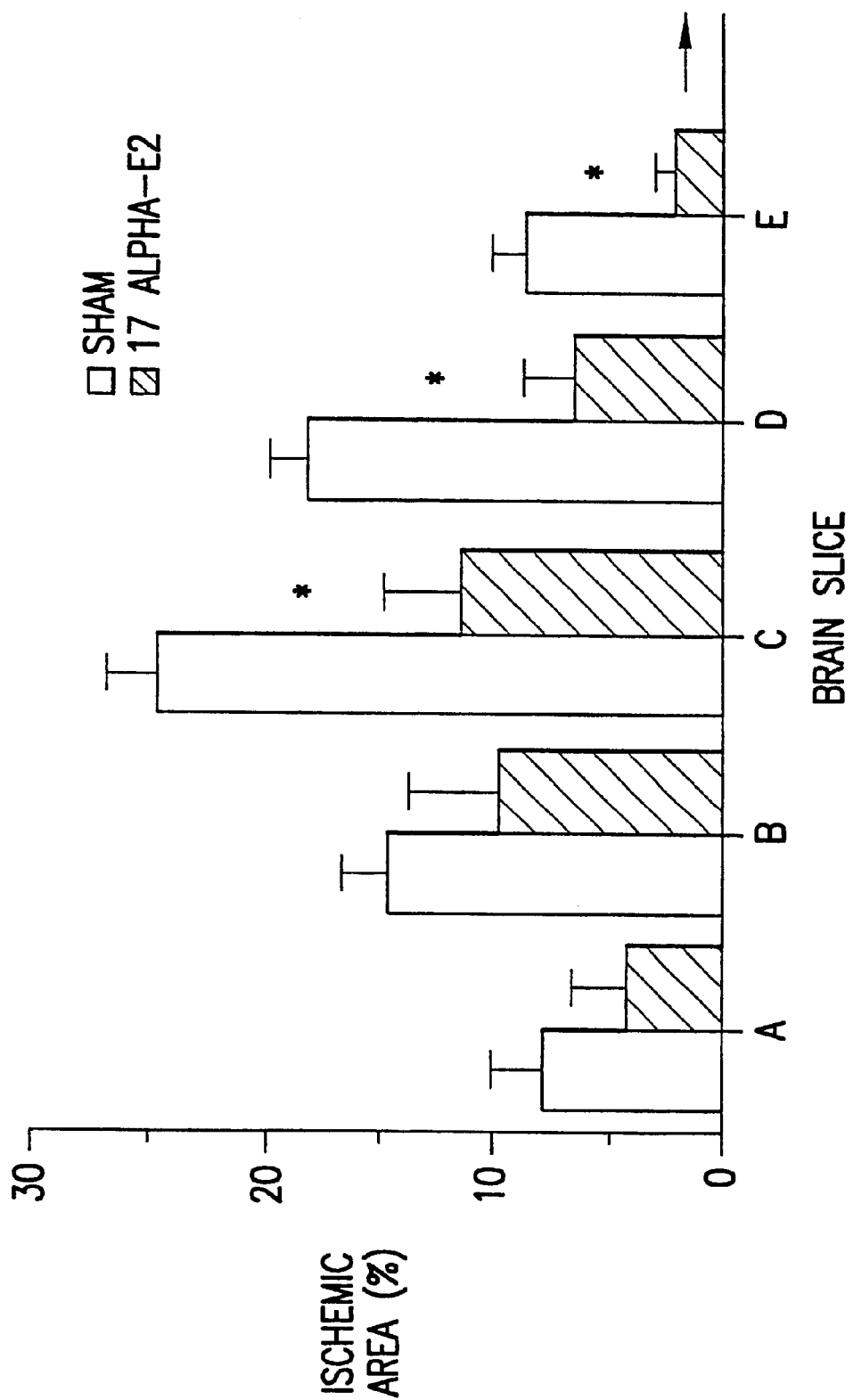

FIG. 3 is a bar graph that shows the effects of pretreatment of ovariectomized rats with 17α-estradiol, initiated 24 hours prior to ischemia induced by MCAO, where the 17α-estradiol is administered in a 5 mm Silastic® tube, and the negative control is a 5 mm Silastic® tube without estrogen (sham). Rats were decapitated 24 hours after the MCAO. Values are given as the mean ±SEM for the percent ischemic area in 5 brain slices. A to E designate the distance caudal to the olfactory bulb A=5 mm, B=7 mm, C=9 mm, D=11 mm, and E=13 mm. *=p<0.05 vs. sham group for the equivalent brain slice; for sham n=10 and for 17α-estradiol groups, n=13.

FIG. 4 is a bar graph that shows the effects of post-treatment of ovariectomized rats with 17β-estradiol or an hydroxypropyl cyclodextrin (HPCD) control at 40 minutes (a) and 90 minutes (b) post onset of MCAO. The 17β-estradiol was formulated in an estradiol chemical delivery system (E2-CDS) at a concentration of 1 mg/kg body weight and injected intravenously. Rats were decapitated 24 hours after the MCAO. Values are given as the mean ±SEM for the percent ischemic area in 5 brain slices. A to E designate the distance caudal to the olfactory bulb A=5 mm, B=7 mm, C=9 mm, D=11 mm and E=13 mm. Where *=p<0.05 vs HPCD group for the same brain slice, N=9 for vehicle, and 13 for E2-CDS groups.

FIG. 5 is a bar graph that shows the effects of 17β-estradiol (2 nM) on brain capillary endothelial cell (BCEC) mortality following 24 hours of hypoglycemia. The control consists of the ethanol vehicle only. The glucose concentrations in the cell media were adjusted from 20 mg % to 200 mg % by adding appropriate amount of D-(+)-glucose to the glucose-free media BCEC were incubated for 24 hours (a) and 48 hours (b). Trypan blue staining was used to distinguish live cells from dead cells. Two cell countings at two different hemacytometer squares were averaged. Mean ±SEM are depicted (n=8–12). *p<0.05 vs. corresponding vehicle control.

Figure 6:
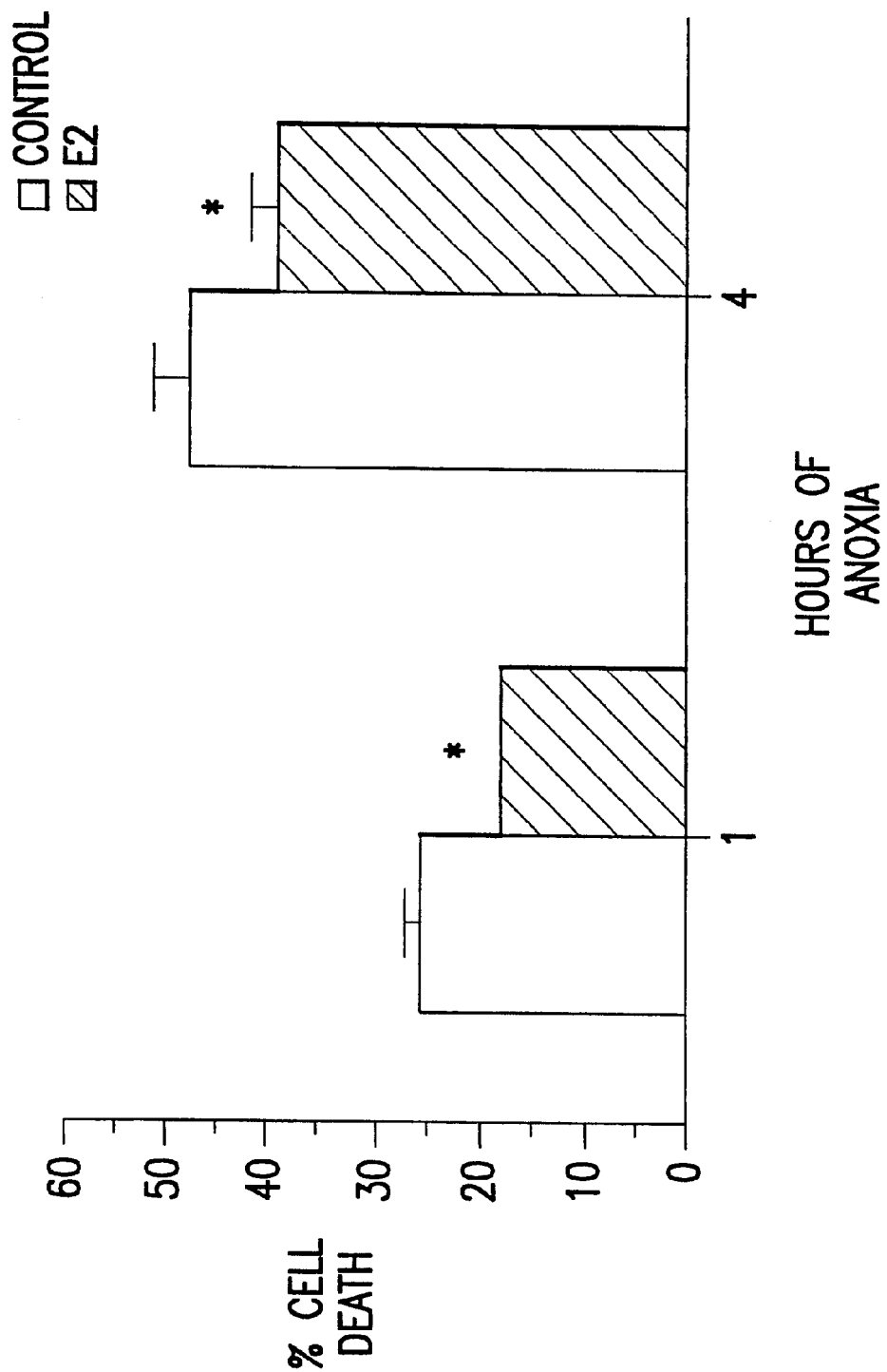

FIG. 6 is a bar graph that shows the effects of 17β-estradiol (2nm) on BCEC mortality following anoxia. The control consists of the ethanol vehicle without estrogen. Cell media contained 200 mg % glucose. Culture dishes containing BCEC were placed in nitrogen filled chamber for 4 hours. Trypan blue staining was used to distinguish live cells from dead cells. Two cell countings at two different hemacytometer squares were averaged. Mean ±SEM are depicted (n=8–12). *p<0.05 vs. corresponding vehicle control.

Figure 7:
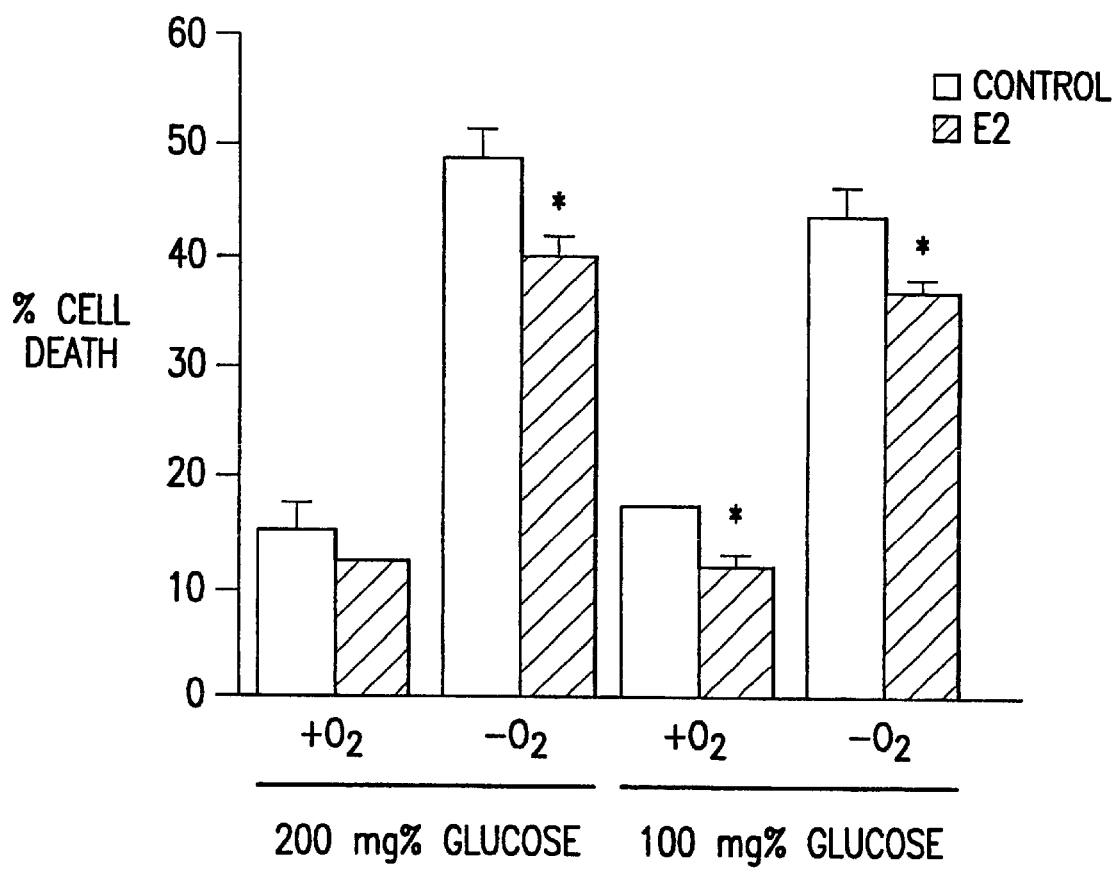

FIG. 7 is a bar graph that shows the effects of 17β-estradiol (2 nm) on BCEC mortality compared with a control (ethanol vehicle) following a combination treatment of both anoxia and hypoglycemia. Cell media contained 200 mg % or 100 mg % glucose. Culture dishes containing BCEC were placed in either an incubator or a nitrogen filled chamber for two hours. Trypan blue staining was used to distinguish live cells from dead cells. Two cell countings at two different hemacytometer squares were averaged. Mean ±SEM are depicted (n=8.12). *<0.05 vs. corresponding vehicle control.

Figure 8:
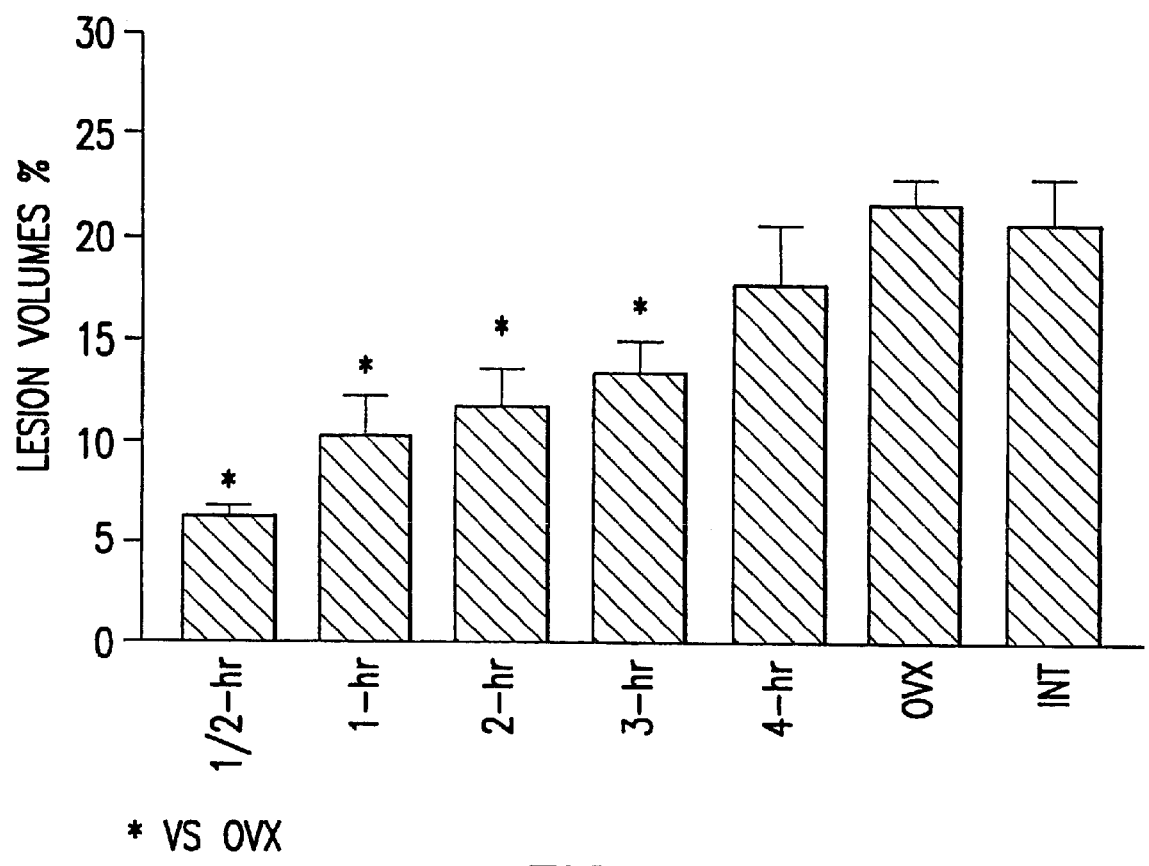

FIG. 8 is a bar graph that shows the effects of post-treatment of ovariectomized (OVX) rats with 17β-estradiol at 0.5 hour, 1 hour, 2 hours, 3 hours or 4 hours following ischemic induced by MCAO. The estrogen compound was administered by a combination of an intravenous preparation (100 μg/kg) of HPCD-complexed 17β-estradiol and Silastic® pellet at the times post-occlusion indicated. Ovariectomized, non-treated animals(OVX) and non-ovariectomized, non-treated animals (INT) were used as controls (n=12 and n=6, respectively). At 48 hours following MCAO, ischemic lesion volume was determined using 2,3,5-triphenyltetrazolium (ITC) staining.

Figure 9:
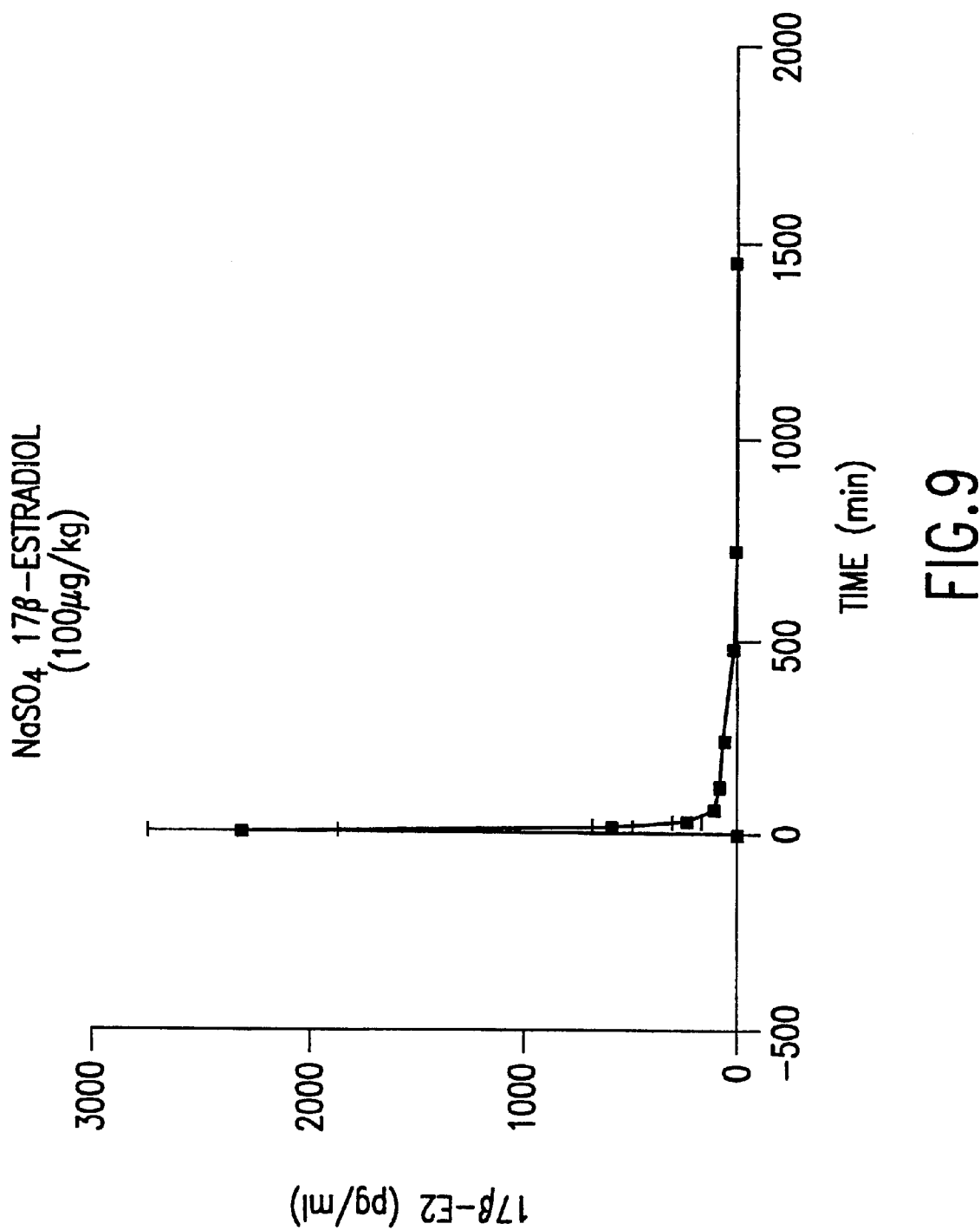

FIG. 9 is a graph that shows the effects on drug kinetics of administering an estrogen compound in single subcutaneous bolus injection in oil on the ordinate, as a function of time on the abscissa.

Figure 10:
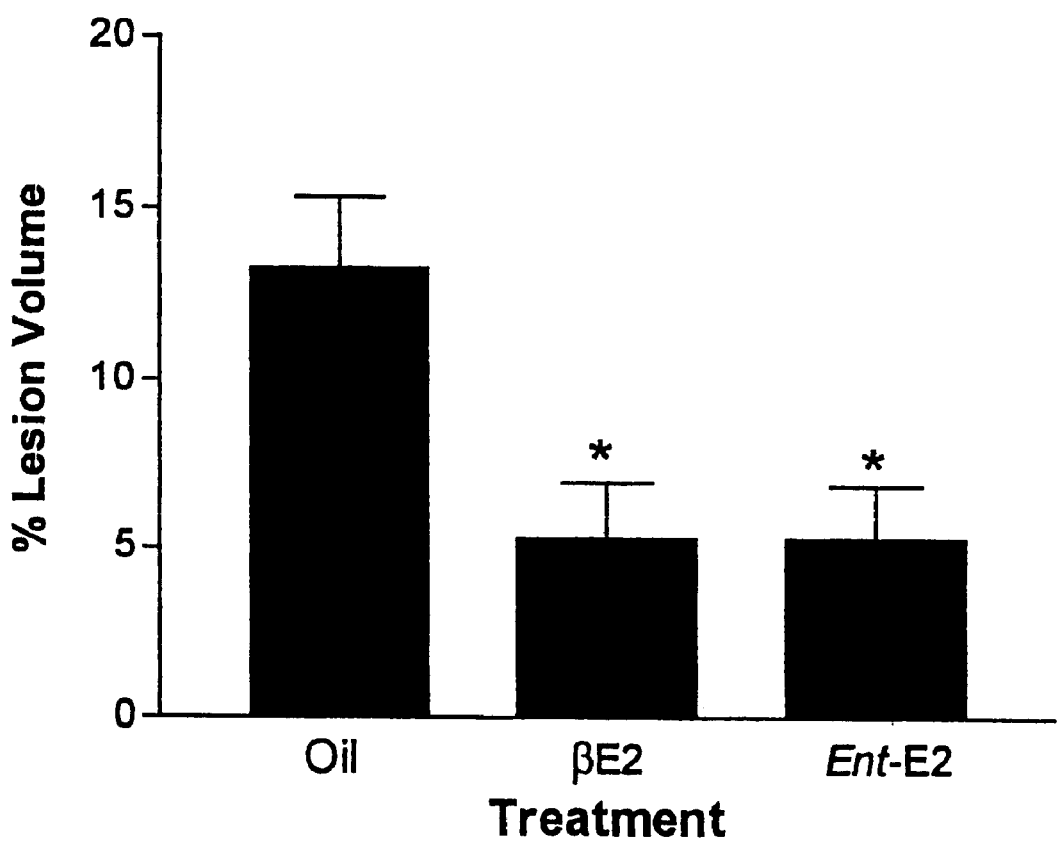

FIG. 10 is a bar graph that shows that in MCAO disease model rats administered agents by subcutaneous injection in oil, ent-17β-estradiol (100 μg/kg body weight) was as effective in reducing the percent lesion volume as 17β-estradiol (100 μg/kg), compared to control animals administered only the oil vehicle (1 mg/kg).

DETAILED DESCRIPTION OF SPECIFIC EMBODIMENTS

There is a need for effective treatments for stroke and other forms of ischemia that are safe, and may be administered preventatively to men and women who are susceptible to such conditions, and may further be used after the ischemia has occurred so as to protect cells from progressive degeneration that is initiated by the ischemic event. There is further a need for therapeutic strategies, to treat victims of stroke or other forms of ischemic events such as myocardial infarction, in which the active drug could enter the bloodstream very rapidly, reach peak levels within minutes, and sustain lower, therapeutic drug dosage levels for a significant period of time (e.g., hours) thereafter.

The invention provides an effective treatment for stroke and other forms of ischemia that may safely be administered to men and women so as to protect cells from progressive degeneration that is initiated by the ischemic event.

Estrogen compounds are defined here and in the claims as any of the structures described in the 11th edition of "Steroids" from Steraloid Inc., Wilton, N.H., incorporated herein by reference. Included in this definition are non-steroidal estrogens described in the aforementioned reference. Other estrogens included in this definition are estrogen derivatives, estrogen metabolites, estrogen precursors, and modifications of the foregoing as well as molecules capable of binding cell associated estrogen receptor as well as other molecules where the result of binding triggers a characteristic estrogen effect. Any diastereomer or enantiomer of compounds described herein is included in the definitions herein. Also included are mixtures of more then one estrogen. The term "estradiol" or "estrogen" is included in the meaning of estrogen compound.

β-estrogen and α-estrogen are isomers of estrogen.

The term "E2" is synonymous with β-estradiol,17β-estradiol, $E_2$, and $β-E_2$.

An "animal subject" is defined here and in the claims is a higher organism including a human subject The term "non-sex hormone" is defined here and in the claims as an estrogen compound having diminished, minimal or no sex-related effect on the subject.

Estrogen compounds are here shown to protect cells from degeneration in the penumbra of the ischemic lesion. (Examples 1 and 2) Estrogen compounds are further shown to be protective of a plurality of cell types, including neuronal cells and endothelial cells (Examples 1–3). According to the invention, estrogen compounds may be used to protect cells from the effects of oxygen deprivation and glucose deprivation and consequently from energy deprivation associated with ischemia.

In an embodiment of the invention, a method of treatment is provided that is suitable for human male and female subjects and involves administering an effective dose of estrogen either before or after a stroke has occurred.

In certain circumstances according to the invention, it is desirable to administer estrogen prior to a predicted ischemic event. Such circumstances arise when, for example, a subject has already experienced a stroke. In this case, the subject will have an increased probability of experiencing a second stroke. Subjects who are susceptible to transient ischemic attacks also have an increased risk of a stroke. Subjects who suffer a subarachnoid hemorrhage may experience further ischemic events induced by vasospasms that constrict the blood vessels. Subjects who experience trauma to organs such as the brain are also susceptible to an ischemic event. The above situations exemplify circumstances when a subject would benefit from pretreatment with an estrogen compound. Such pretreatment may be beneficial in reducing the adverse effects of a future ischemic event when administered in the short term, such as within 24 hours before the event (Example 1) or in the long term, where administration begins immediately after an event such as a stroke and continues prophylactically for an extended period of time. An example of time of administration for prophylactic use may extend from days to months depending of the particular susceptibility profile of the individual. In these circumstances, a course of at least one dose of estrogen may be administered over time so that an effective dose is maintained in the subject. For short term treatments, parenteral administration may be used as an alternative to the delivery of a dose by any of the routes specified below. The optimal dose of estrogen compound for prophylactic use should provide a plasma concentration of 10–500 $\mu$g/ml of estrogen compound, however higher doses are also acceptable. In these circumstances, the use of non-sex estrogen compounds such as the α-estrogen isomers are of particular utility in men and women because the sex-related functions of the hormone are avoided.

According to embodiments of the invention, estrogen compounds are effective in reducing the adverse effects of an ischemic event such as cerebrovascular disease, subarachnoid hemorrhage, or trauma. Accordingly, the compound is administered as soon as possible after initiation of the event and preferably within 12 hours, more particularly, within 5 hours following the event. It is desirable that an increased concentration of estrogen compound be maintained in the plasma for at least several hours to several days following the ischemic event. The increased concentration of estrogen compound in the plasma should be in the range of 10–12,000 pg/ml of estrogen compound.

The present invention demonstrates for the first time that pretreatment with estrogens or early post-treatment of an estrogen compound can significantly reduce the size of the necrotic area following an ischemic event. This effect of pretreatment with an estrogen compound is independent of the isomeric form and the route of administration of the estrogen compound. α-isomers of estrogen have been shown to be as effective as β-isomers of estrogen in protecting cells from the effects of ischemia. The method as exemplified in Example 1 and FIGS. 1, 2 and 3 confirm that the protective activity of estrogen compounds is not dependent on the sex-related activity of the hormone (estrogenicity). α-isomers of estrogen compounds are non-sex hormones, yet these compounds are as effective at protecting the brain against ischemic damage as the β-isomers. Example 1 further demonstrates that the observed reduction in mortality of ovariectomized rats when treated with 17β-estradiol is not dependent on the route of administration, since the protective effect was similar when the same estrogen compound was administered as a subcutaneous implant or as an intravenous injection. Regardless of the route of administration or the formulation, the estrogen compounds have a remarkable effect on the ability of animals to survive an ischemic event.

The demonstration that estrogen is efficacious in protection of cells in an ischemic area is demonstrated in the examples below using rat models in which the middle cerebral artery (MCA) is experimentally occluded, the middle cerebral artery occlusion (MCAO) model. This animal model is well known in the art to simulate an in vivo ischemic event such as may occur in a human subject. The experimental occlusion of the MCA causes a large unilateral ischemic area that typically involves the basal ganglion and frontal, parietal, and temporal cortical areas (Menzies et al. Neurosurgery 31, 100–106 (1992)). The ischemic lesion begins with a smaller core at the site perfused by the MCA and grows with time. This penumbral area around the core infarct is believed to result from a propagation of the lesion from the core outward to tissue that remains perfused by collateral circulation during the occlusion. The effect of a therapeutic agent on the penumbra surrounding the core of the ischemic event may be examined when brain slices are obtained from the animal. The MCA supplies blood to the cortical surfaces of frontal, parietal, and temporal lobes as well as basal ganglia and internal capsule. Slices of the brain are taken around the region where the greatest ischemic effect occurs. These regions have been identified as region B, C, and D in Examples 2 and 3. These regions are not as readily compensated by alternative sources of blood flow as are regions A and E. This is because the MCA is the terminal artery on which the lace of collateral arteries supplying the MCA-distributed area relies, thereby making the MCA-occlusion induced ischemia uncompensatible. On the other hand, anastomoses between MCA and the anterior carotid artery (ACA) in region A and between MCA and the posterior carotid artery (PCA) in region E (Examples 1 and 2), may compensate for the MCA occlusion-induced ischemia as observed in the present study.

In order to study the effect of estrogen on the propagation of the lesion following an ischemic event, rats were ovariectomized and two weeks later were exposed to various estrogen preparations prior to or following MCAO. (Examples 1 and 2). Untreated, ovariectomized rats had a mortality of 65%. Pretreatment with E2-CDS or 17β- estradiol itself decreased mortality from 16% and 22%, respectively. This marked reduction in mortality was accompanied by a reduction in the ischemic area of the brain from 25.6±5.7% in the untreated, ovariectomized rats to 9.1±4.2% and 9.8±4.0 in the E2-CDS or 17β-estradiol treated rats, respectively. Similarly, pretreatment with non-sex hormones, exemplified by 17α-estradiol, reduced ischemic area by 55 to 81% (Example 1). When administered 40 or 90 minutes after MCAO, 17β-estradiol reduced ischemic area by 45–90% or 31%, respectively (Example 2). Non-sex hormones were also highly protective when administered following induction of ischemia These results demonstrate the neuroprotective effect of estrogen compounds in the brain following an ischemic event.

Reduction in available oxygen and glucose for energy metabolism is a feature of an ischemic event. This has a negative impact on the blood vessels that may be required to supply nutrients once the occlusion is reversed. The negative effect on blood vessels following ischemia further increases the long-term damage associated with the event. This effect can be reproduced in vitro as described in Example 3. In these circumstances, it has been shown here, estrogen compounds are capable of protecting brain capillary endothelial cells from cell death that would otherwise occur during hypoglycemia and anoxia during an ischemic event (FIGS. 5–7). As a consequence of this protection, the integrity of the vascular supply and the blood brain barrier is preserved by estrogen compounds such that following reperfusion of the brain after the ischemic event, blood flow and transport functions can once again occur.

Estrogen compounds are shown here to be effectively delivered subcutaneously in an oil vehicle (Example 5 and FIG. 9). This mode of delivery was successful at achieving blood levels of 4,610 pg/ml of the estrogen compound within 30 minutes. Sustained delivery was achieved also, as animal blood levels of 2,004 pg/ml was at the four hour time point (FIG. 9).

Synthesis of ent-17β-estradiol is shown by the methods of Example 6, and in Table 3. FIG. 10 and Example 7 shows that ent-17β-estradiol was as effective a therapeutic agent as 17β-estradiol.

EXAMPLES

Example 1

Measurement of the effect of estrogen compound administered prior to ischemic events Rats were used as experimental models to test the effects of estrogen compounds in protecting against ischemic damage. To remove the naturally occurring source of estrogen, ovariectomies were performed prior to induction of ischemia.

Subsequent to the ovariectomy, rats were treated with an estrogen compound either by subcutaneous delivery with Silastic® tubes 24 hours prior to the MCA occlusion or by intravenous delivery as follows:

Subcutaneous sustained delivery: 17β- or 17α-estradiol was packed into 5 mm long Silastic® tubes (Dow-Corning, Midland, Mich.) according to the method of Mohammed et al. 1985 Ann. Neurol 18, 705–711. Sham (empty) tubes were similarly prepared as estrogen negative controls. The pellets were implanted subcutaneously (sc) into ovariectomized rats 24 hours prior to MCAO. 5 mm of Silastic® tubing containing estrogen resulted in plasma levels of about 100–200 pg/ml.

Intravenous (iv) delivery: 17β-estradiol was prepared for iv delivery using an estrogen-chemical delivery system (E2-CDS) as described in Brewster et al., Reviews in the Neurosciences 2, 241–285 (1990) and Estes et al., Life Sciences 40: 1327–1334 (1987). E2-CDS was complexed with hydroxypropyl- -cyclodextrin (HPCD) (Brewster et al. J. Parenteral Science and Technology 43: 231–240, (1989)). The complexation achieved was 32 mg of E2-CDS per gram HPCD. In the first study, a single iv injection of E2-CDS (1 mg/kg body weight) was administered at 24 hours prior to MCAO. The control was administered HPCD only. The chemical delivery system is formulated so that the estrogen is slowly released from the carrier. This delivery system has been shown to effectively deliver estrogen in a sustained manner to the brain. Indeed, the dose of E2-CDS used in Examples 1 and 2 (1 mg/kg) is sufficient to provide 1000 pg/gm brain tissue at 24 hours post administration.

At 7 to 8 days after ovariectomy, a method for occluding the middle carotid artery was applied to the rat using modifications of the methods of Longa et al. (1989) Stroke, vol. 20, 84–91; and Nagasawa et al. (1989) Stroke, vol.20, 1037–1043, with certain modifications, as described herein.

Animals were anesthetized by ip injection with ketamine (60 mg/kg) and xylazine (10 mg/kg). Rectal temperature was monitored and maintained between 36.5 and 37.0 C with a heat lamp throughout the entire procedure. The left carotid artery was exposed through a midline cervical incision. The left sternohyloid, sternomastoid, digastric (posterior belly) and the omohyloid muscles were divided and retracted. Part of the greater horn of the hyloid bone was cut to facilitate exposure of the distal external carotid artery (ECA). The common carotid artery (CCA), ECA, and internal carotid artery (ICA) were dissected away from adjacent nerves. The distal ECA and its branches, the CCA, and the pterygopalatine arteries were coagulated completely. A microvascular clip was placed on the ICA near skull base. A 2.5 cm length of 3-0 monofilament nylon suture was heated to create a globule for easy movement and blocking of the lumen of the vessel. This was introduced into the ECA lumen through the puncture. The suture was gently advanced to the distal ICA until it reached the clipped position. The microvascular clip was then removed and the suture was inserted until resistance was felt. The distance between the CCA bifurcation and the resistive point was about 1.8 cm. This operative procedure was completed within 10 minutes without bleeding. After the prescribed occlusion tine (40 minutes), the suture was withdrawn from the ICA and the distal ICA was immediately cauterized.

Animals that survived until the scheduled sacrifice time were sacrificed by decapitation. Scheduled post-ischemic sacrifices occurred at 6 hours, 24 hours and 1 week post MCAO (Table 1). For the 6-hour sample, animals were monitored continuously. For the 24-hour sample, animals were observed for about 4 hours and were then returned to their cages. Similarly, animals scheduled for the 1 week post-ischemic sacrifice were monitored for the first 4 hours after surgery and then daily thereafter.

The brains were isolated from the decapitated heads, sliced into 3 or 5 coronal tissue slices as described below and then stained with hematoxylin and eosin to determine the extent of the ischemic area Stained slices were photographed and subsequently imaged using a Macintosh Cadre 800 computer, equipped with an Image 1.47 software program for the assessment of the cross-sectional area of the ischemic lesion. These images and the calculated area of ischemic damage were stored in the program for later retrieval and data reduction. The significance of differences in mortality among the different treatment groups was determined using Chi-Square analysis.

The results obtained using different routes of administration and different isomeric forms of estrogen compounds are provided below.

The administration of an estrogen compound by subcutaneously using Silastic® tubes or by controlled intravenous delivery, at 24 hours prior to the ischemic event, caused brain lesion size and mortality to be reduced.

Figure 1:
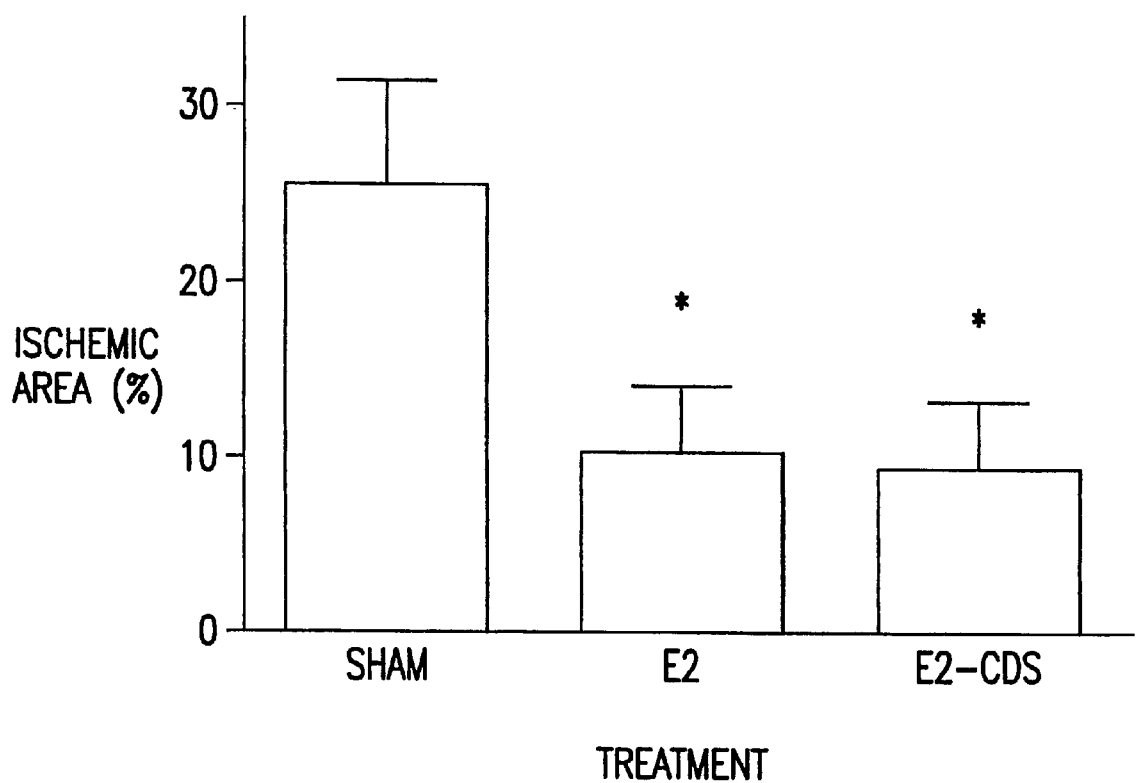

Three coronal slices were made at 1, 5, and 7 mm posterior to the olfactory bulb. Only 35% of the control (sham) animals survived until the scheduled post-ischemic sacrifice time (Table 1). In contrast, 78% and 84% of animals, treated 24 hours prior to MCAO with either 17β-estradiol in a Silastic® tube (E2 implant) or with E2-CDS at 1 mg/g administered by iv injection survived until the scheduled post-ischemic sacrifice time at 6 hours, 1 day, and 1 week. Elevated levels of 17β-estradiol were detected in all samples at the time of sacrifice. The reduction in mortality in the estrogen compound pretreatment group was most notable at 1 day and 1 week after MCAO (Table 1). Furthermore, the reduced mortality in the estrogen compound treated rats was correlated with the reduction of ischemic area in animals that survived to the scheduled 1 day or 1 week post-ischemic sacrifice time (FIG. 1). Control (sham) rats had ischemic lesions that occupied 25.6±5.7% of the cross-sectional area of brain sections evaluated (FIG. 1). By contrast, rats treated with 17β-estradiol in Silastic® tubes or E2-CDS had ischemic lesions that occupied only 9.8±4.0 and 9.1±4.2%, respectively, of the brain area evaluated. The significance of differences among groups was determined by analysis of variance (ANOVA) and the Fischer's test was used for the post hoc comparison. Determination of areas under the curves were not done here as only three brain slices were taken.

The results shown in FIG. 2 illustrate the significant protective effect of estrogen compounds in tissue slices A–D in animals treated with subcutaneous injection of 17β-estradiol (10 μg/ml) two hours prior to an ischemic event.

Rats were ovariectomized, treated with a single dose of 17β-estradiol (10 μg/kg) administered by sc injection, 14 days after the ovariectomy and two hours prior to the ischemic event as described above. This injection was sufficient to achieve a plasma concentration of 250 pg/ml at the time of occlusion. The animals were sacrificed at 24 hours and the brains extracted. Estrogen compound replacement of ovariectomized rats reduced by 46.3% and 44.1% ($p<0.05$) ischemic lesion size of the whole coronal section at region C and D, respectively (FIG. 2). These regions correspond to sections taken at 9 and 11 mm caudal to the olfactory bulb.

The results shown in FIG. 3 illustrate the significant protective effect of 17α-estradiol in tissue slices A–E in animals treated with a sustained subcutaneous delivery of 17α-estradiol initiated 24 hours prior to the ischemic event.

Ovariectomized rats were treated with 5 mm Silastic® tubes containing 17α-estradiol at 24 hours prior to MCAO. At 24 hours after the MCAO, the animals were sacrificed and the brains extracted. Five, 2 mm thick coronal sections were made at 5, 7, 9, 11, and 13 mm posterior of the olfactory bulb. The slices were then incubated for 30 minutes in a 2% solution of 2,3,5-triphenyl tetrazolium (ITC; Sigma Chemical Corp., St. Louis, Mo.) in physiological saline at 37 C. Sham-treated rats showed the expected ischemic lesion, with the maximum ischemic area (24.1±2.4%) occurring in slice C (9 mm posterior to the olfactory bulb) and smaller lesion areas occurring in more rostral and caudal slices (FIG. 3). The significance of differences between sham and steroid-treated groups, were thus determined and data from two groups were compared for each experiment. To determine the area under the lesion curve for a given treatment, the trapezoidal method was used. Areas calculated for each animal were grouped and the differences between groups were determined by the student t test.

Animals pretreated with 17α-estradiol exhibited smaller ischemic areas compared with the sham treated animals in all slices evaluated (FIG. 3, A–E). Specifically, slices C, D and E (sections taken at 7, 9, and 11 mm posterior to the olfactory bulb), ischemic area was reduced significantly by 55%, 66%, and 81%, respectively (FIG. 3). The area under the ischemic lesion curve for the sham-treated, and the 17α-estradiol groups was 8.1±0.8 and 3.7±1.3, respectively (Table 2).

Example 2

Measurement of the effect of estrogen compounds administered after the ischemic event To test the extent to which estrogen treatment was effective after the onset of the occlusion, ovariectomized rats were treated iv with a sustained release of either E2-CDS or with a control (HPCD vehicle), the positive sample causing a brain tissue concentration of estrogen of 1000 pg estrogen/gm brain tissue, 24 hours after administration. The estrogen compound was administered at 40 minutes and 90 minutes after the onset of the MCAO (FIGS. 4a and b, Table 2) and the animals sacrificed at 24 hours after the MCAO. Five 2 mm thick coronal sections were made at 5, 7, 9, 11, and 13 mm posterior of the olfactory bulb as described in Example 1.

Figure 4A:
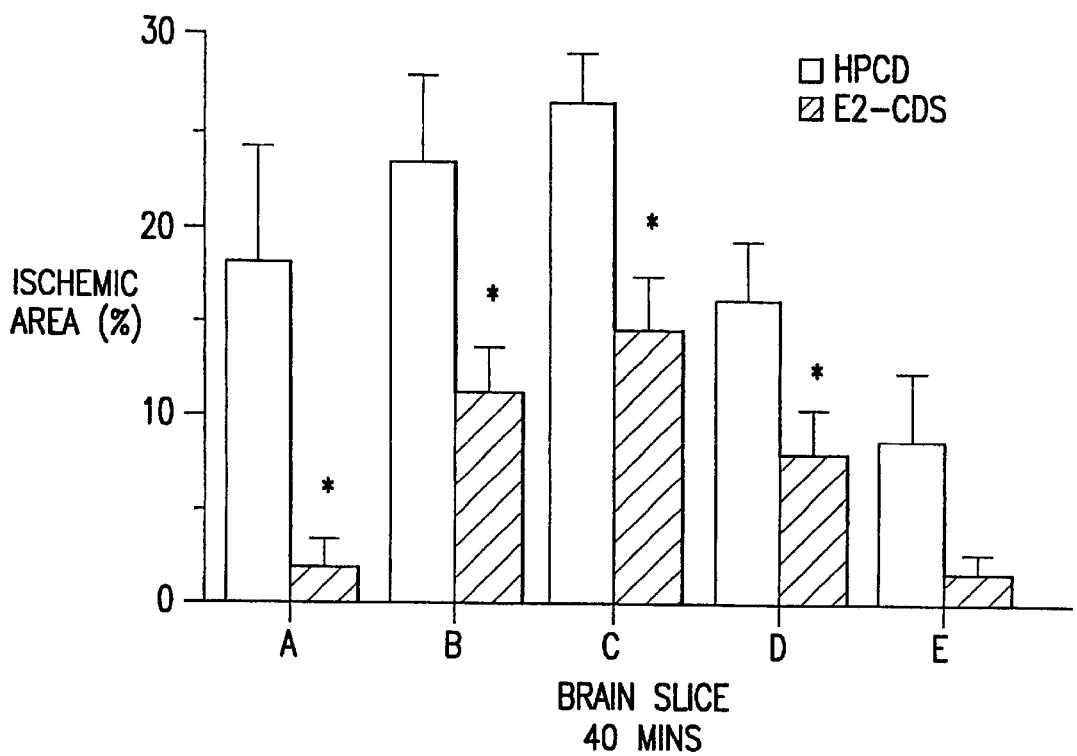

Post-treatment at 40 minutes: As shown in FIG. 4a, the control rats (HPCD treated) had large ischemic areas in all slices sampled, with the maximum ischemic area of 25.6±2.7% observed in slice C. E2-CDS treatment reduced ischemic area in all slices sampled (FIG. 4). The extent of reduction in ischemic area ranged from 90% in slice A (5 mm posterior of the olfactory bulb) to 45% in slice C (9m posterior to the olfactory bulb) (FIG. 4a). The integrated area under the ischemic lesion curve was 10.1±1.6 for the vehicle treated rats and 4.5±0.9 for the E2-CDS animals (Table 2).

Figure 4B:
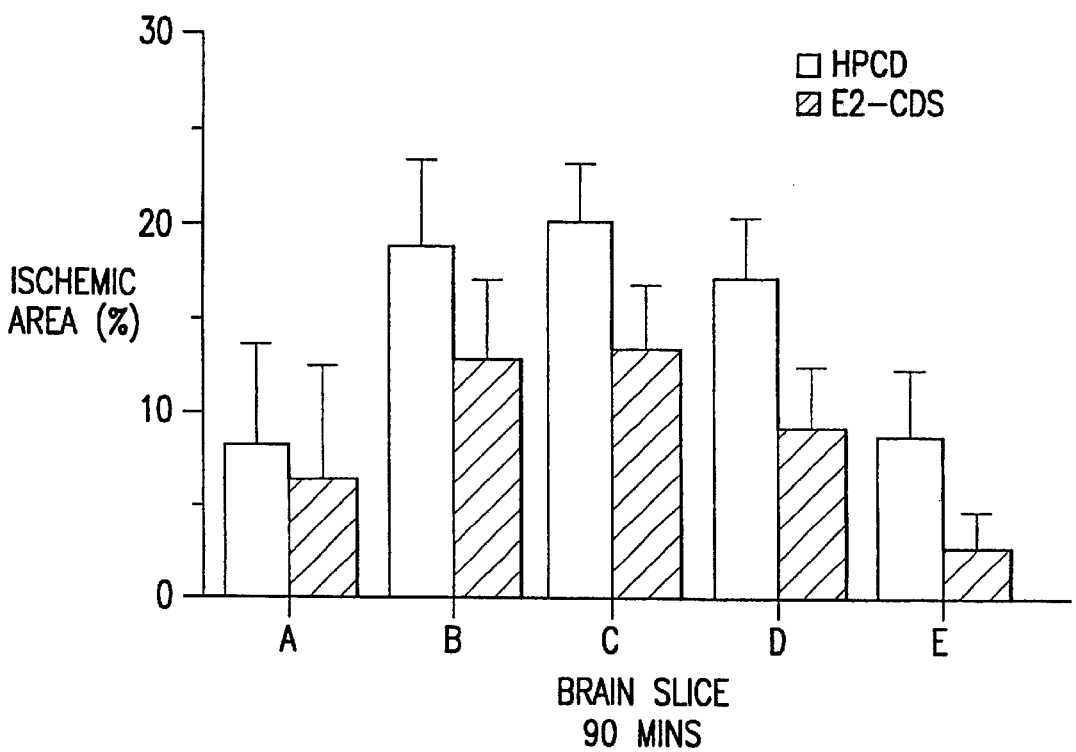

Post-treatment at 90 minutes: Rats were treated with E2-CDS or HPCD vehicle at 90 minutes after the onset of the occlusion (FIG. 4b and Table 2). Again, HPCD treated animals showed a large lesion in all slices sampled, with the maximum ischemic area seen in slice C (20.5±3.1% of the slice area). Treatment with E2-CDS reduced the mean ischemic area in all slices examined, however, the differences were not statistically significant. An evaluation of the area under the ischemic curve for the two groups revealed that treatment with E2-CDS reduced the ischemic area by 37.1%, from 8.2±1.7 (HPCD treated animals ) to 5.2±1.7 (E2-CDS treated animals).

Example 3

Estrogen compounds protect brain capillary endothelial cells under conditions associated with focal ischemia Primary rat brain capillary endothelial cells (BCEC) cultures were prepared following the method of Goldstein, J. Neurochemistry vol. 25, 715–717, 1975, incorporated herein by reference.

Hypoglycemia experiments were undertaken. 17β-estradiol (2 nm) or control (ethanol vehicle) were added to BCEC cultures. The glucose concentration of the culture media was then adjusted from 20 mg % to 200 mg % by adding appropriate amount of D-(+)-glucose to the glucose-free media and monitored by Glucose and L-Lactate Analyzer (YSI model 2300 STAT plus, YSI, Inc., Yellow Springs, Ohio). The hypoglycemic cultures were maintained for 24 hours or 48 hours prior to staining with Trypan blue.

Anoxia environment was created by placing culture dishes containing BCEC with or without 2 mm 17β-estradiol in the Modular Incubator Chamber (Billups-Rothenberg, Inc., Delmar, Calif.). Nitrogen gas was influxed to replace the oxygen inside the chamber. The chamber was sealed and placed in the incubator for four hours for nonhypoglycemic cultures and 2 hours for hypoglycemic cultures.

Cell mortality was counted using Trypan blue staining method. Cell death percentage was calculated as dead cell/alive cell×100%.

Statistical methods used included two-way analysis of variance, applied to determine the significance of the difference among the experimental groups. Kruskal-Wallis nonparametric analysis was used for data presented as percentage. The Mann-Whitney U tests were used when Kruskal-Wallis showed significance among groups. $P<0.05$ was considered significant.

Figure 5A:
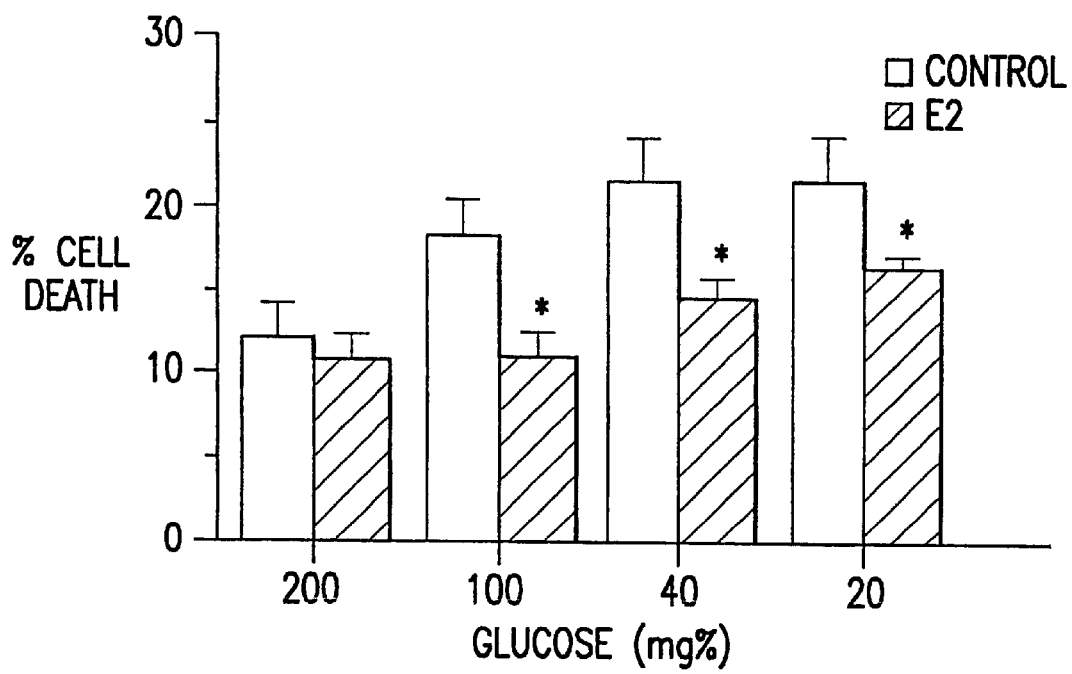
Figure 5B:
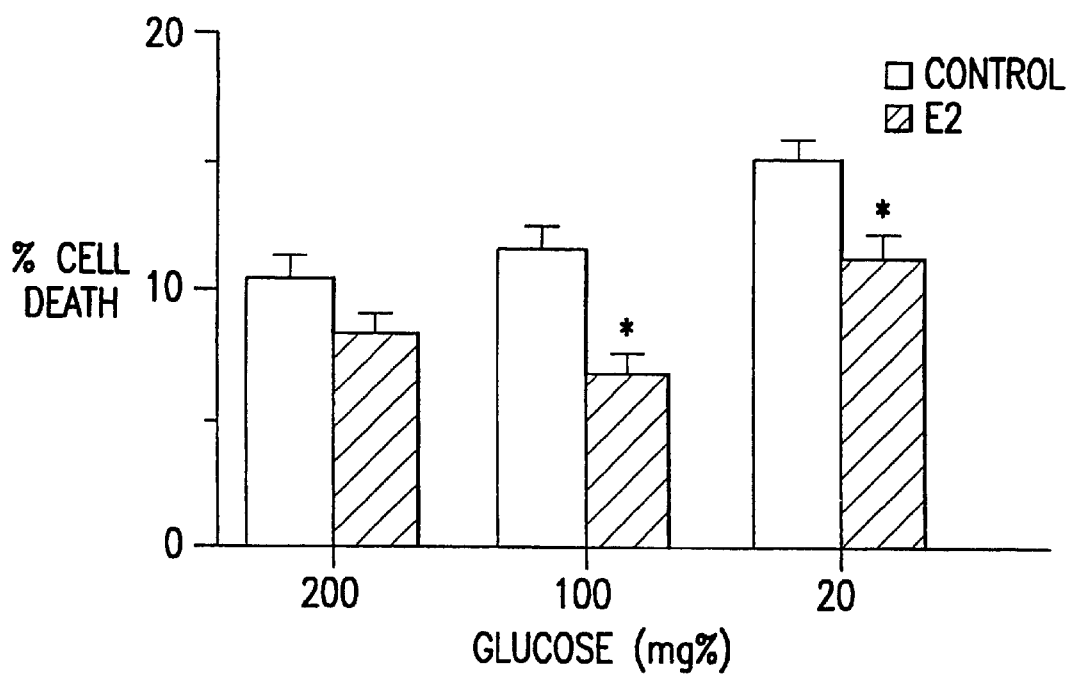

The results are shown in FIGS. 5a and 5b for cells deprived of glucose. The normal glucose concentration in the media is 200 mg per 100 ml (200 mg %). Little difference was observed in percent cell death between cultures with and without estrogen supplement at this glucose concentration. However, reduction in medium glucose content to 100 mg %, 40 mg %, and 20 mg % caused cell death, and 17β-estradiol saved cell loss by 35.9%, 28.4% and 23.% (p<0.05), respectively, compared with corresponding control groups not exposed to the estrogen compound. It was further noted that there were floating cells, which meant more dead cells, in the control groups than in the estradiol-treated groups. Since these cells were excluded when counting cell mortality, the protective effects of estradiol may be underestimated. A similar beneficial effect was observed over a 24 hour and 48 hour hypoglycemic treatment (FIGS. 5a and b, respectively).

Anoxia had a more dramatic effect in cell viability as shown in FIG. 6 for cells in media containing 200 mg % glucose. Anoxia induced cell death as much as 48.8% and 39.8% in the control and E2 reduced cell death by 28.4% (p<0.05) at 1 hour and 18.4% (p<0.05) at 4 hour anoxic insults.

When cells were exposed to both hypoglycemia (100 mg % hypoglycemia) and anoxia conditions (2 hours), 17β-estradiol was effective in protecting cultured BCEC from the cumulative effect of both conditions (FIG. 7).

The in vitro assay is representative of events that follow ischemia such as that induced by MCAO where oxygen and glucose supplies to the of the blood brain barrier endothelial cells are reduced.

Example 4

Comparison of post-treatment at 0.5, 1, 2, 3 and 4 hour time points

Ovariectomized rats were treated with both an iv injection (100 μg/kg) of HPCD-complexed 17β-estradiol and a 17β-estradiol containing Silastic® pellet at the times indicated after the onset of occlusion (FIG. 8). HPCD and HPCD-encapsulated 17β-estradiol were purchased from Sigma (St Louis, Mo.). Ovariectomized, non-treated animals (OVX) and non-ovariectomized, non-treated animals (INT) were used as controls (n=12 and n=6, respectively). At 48 hours following MCAO, animals were sacrificed and ischemic lesion volume was determined by obtaining brain sections as previously described and staining with TTC. FIG. 8 shows that significant protection was observed when drugs were administered at 0.5, 1, 2, or 3 hours post-occlusion.

Example 5

Delivery of an estrogen compound using an oil vehicle

To test the kinetics of uptake of an estrogen compound in an oil vehicle, male Sprague-Dawley rats (Taconic) were given 17β-estradiol by sc injection, and drug levels in the blood were determined over a 25 hour period. The drug was dissolved in corn oil at 100 μg/ml and the final dosage delivered was 100 μg/kg. Blood samples were drawn at 30 minutes prior to drug administration, 30 minutes after drug administration, 4 hours after drug administration and 24 hours after drug administration. Venous blood was collected into heparinized tubes, centrifuged and the plasma was collected and frozen levels of 17β-estradiol were determined using a commercially supplied radioimmunoassay kit.

As shown in FIG. 9, there was a significant, very rapid uptake of the 17β-estradiol into the bloodstream, peaking in this experiment at the 30 minute time point (at 4,610 pg/ml). At 4 hours, the level of circulating 17β-estradiol was 2,004 pg/ml. By 25 hours, 17β-estradiol blood levels had fallen off to near zero.

These delivery kinetics indicate that the delivery vehicle described here in which the estrogen compound was dissolved in oil and delivered by a single subcutaneous injection into animals serves the dual purpose of initiating rapid uptake of the compound into the blood, and providing for sustained delivery of the compound for hours thereafter.

Example 6

Synthesis of ent-17β-estradiol

The synthesis of ent-17β-estradiol is summarized in Table 3. The known starting material, [3R-(3α,3aα,9aα,9bβ)]-3-(1,1-dimethylethoxy)-1,2,3,3a,4,5,8,9,9a,9b-decahydro-3a-methyl-6-[2-(2-methyl-1,3-dioxolan-2-yl)ethyl-7H-benz[e]inden-7-one (Chemical Abstracts Registry Number, 139973-49-2), was prepared by a multistep synthetic pathway as described in the literature (Rychnovsky, S. D. et al. J. Org. Chem. 1992 vol.57, 2743–2736). This compound was then converted in either of two ways (Method A or Method B) to ent-19-nortestosterone (Chemical Abstracts Registry Number, 4091-86-5).

In the first step of Method A, the double bond is reduced using lithium in liquid ammonia and the resulting tricyclic compound is cyclized to ent-19-nortestosterone in the second step. In the first step of Method B, the double bond is reduced by catalytic hydrogenation and the resulting tricyclic compound is again cyclized to ent-19-nortestosterone in the second step. Method B has been previously used to prepare 19-nortestosterone (Micheli, R. A. et al., 1975 J. Org. Chem. Vol.40, 675–681). The hydroxy group of ent-19-nortestosterone is then esterified and the A-ring of the steroid is aromatized using $CuBr_2$ in acetonitrile. This reaction has been reported previously for the conversion of 19-nortestosterone,17-acetate to 17β-estradiol,17-acetate (Rao, P. N. et al. 1994, Steroids vol.59, 621–627). Finally, the 17-acetate group is removed by saponification to give ent-17β-estradiol (Chemistry Abstracts Registry Number, 3736-22-9). The structure of ent-17β-estradiol was proven by experimental data, which showed that the compound had the same melting point, IR, $^1$H NMR and $^{13}$C NMR spectra, but opposite optical rotation as 17β-estradiol.

A. Preparation of (8α,9β,10α,13α,14β,17α)-17-hydroxyestr-4en-3-one (ent-19-nortestosterone).

Method A.

Ammonia gas was condensed in a 500 ml three-necked round bottom flask cooled to −78° C. (cooling bath: dry ice, 2-propanol) under nitrogen until 200 ml of liquid ammonia was collected. Freshly cut lithium (1.4 g, 200 mmol) was added and the reaction solution was stirred (overhead mechanical stirrer) for 15 minutes. To the blue colored reaction solution, [3R-(3α,3aα,9aα,9bβ)]-3-(1,1-dimethylethoxy)-1,2,3,3a,4,5,8,9,9a,9b-decahydro-3a-methyl-6-[2-(2-methyl-1,3-dioxolan-2-yl)ethyl-7H-benz[e]inden-7-one (4 g, 10 mmol) in dry tetrahydrofuran (THF; 100 ml) was added and the reaction solution was stirred for 1 hour. The blue color persisted during this time. After 1 hour, solid ammonium chloride (5 g) was added slowly and carefully while maintaining the temperature at −78° C. The blue colored solution turned into a milky white solution on addition of the ammonium chloride. The cooling bath was removed and the reaction mixture was then left overnight during which time the liquid ammonia became gaseous ammonia and evaporated. Water (200 ml) was added and the reaction mixture was extracted with ethyl acetate (3×100 ml). The combined ethyl acetate extracts were washed with brine (100 ml). The solvents were removed and the residue obtained was chromatographed on a silica gel column eluted with 20% ethyl acetate in hexanes to give pure [3R-(3α,3aα,5aβ,6β,9aα,9bβ)]-3-(1,1-dimethylethoxy)-dodecahydro-3a-methyl-6-[2-(2-methyl-1,3-dioxolan-2-yl)ethyl-7H-benz[e]inden-7-one (3 g, 75%). A portion of this material was then converted into ent-19-nortestosterone as described below. To the above [3R-(3α,3aα,5aβ,6β,9aα,9bβ)]-3-(1,1-dimethylethoxy)-dodecahydro-3a-methyl-6-[2-(2-methyl-1,3-dioxolan-2-yl)ethyl-7H-benz[e]inden-7-one (2 g, 5.12 mmol) in methanol (100 ml), 3N hydrochloric acid (30 ml) was added and the reaction solution was refluxed for 24 hours. The reaction solution was then poured into water and the aqueous reaction mixture was extracted with ethyl acetate (2×100 ml). The combined extracts were washed with brine. The crude product was chromatographed on a silica gel column eluted with 20% ethyl acetate in hexanes mixture to give pure ent-19-nortestosterone (0.5 g, 57%) as a white crystalline solid which had physical properties identical to those reported below when this compound was prepared using Method B.

Method B.

[3R-(3α,3aα,9aα,9bβ)]-3-(1,1-Dimethylethoxy)-1,2,3,3a,4,5,8,9,9a,9b-decahydro-3a-methyl-6-[2-(2-methyl-1,3-dioxolan-2-yl)ethyl-7H-benz[e]inden-7-one, 18.35 g, 47 mmol) was dissolved in ethanol (EtOH; 180 ml) in a Parr hydrogenation bottle used with a Parr hydrogenation apparatus. Pd/C catalyst (1.00 g, 9.4 mmol) was added, air was removed, the reaction vessel was pressurized to 60 psi with hydrogen gas and the rocker motor was started. The hydrogenation reaction was carried out for 4 hours. At the conclusion of this time, the reaction mixture was filtered through a bed of Celite. Solvent removal gave an oil which was used immediately in the next step.

The oil was dissolved in EtOH (50 ml) and 6N HCl was added (50 ml). The reaction solution was then refluxed. After 48 hours, the reaction mixture was neutralized by the addition of solid NaHCO$_3$ until the pH was 8–9. Volatile solvents were removed and the aqueous residue was extracted with methylene chloride (3 portions of 200 ml each). The organic extracts were combined, dried with MgSO$_4$, filtered, and the solvents were removed to afford an oil (12.5 g). $^1$H NMR analysis revealed a complex mixture of products. Purification by column chromatography (silica gel eluted with 19–37% ethyl acetate in hexanes), followed by recrystallization gave ent-19-nortestosterone (2.04 g, 7.45 mmol, 16% yield): [α]=−57.3° (c=0.99, CHCl$_3$); mp 124–125° C.; IR 3425, 2926, 2866, 1661, 1619, 1450, 1334, 1261, 1208, 1135, 1056 cm$^{-1}$; $^1$HNMR (300 MHz, CDCl$_3$) δ5.81 (1 H, s), 3.65 (1 H, t, J=8.4 Hz), 2.5–2.0 (7 H, m), 1.90–1.75 (3 H, m), 1.70–0.80 (11 H, m), 0.79 (3 H, s); $^{13}$C NMR (75 MHz, CDCl$_3$) δ200.05, 166.72, 124.64, 81.66, 49.70, 49.53, 42.93, 42.52, 40.43, 36.39, 36.33, 35.37, 30.59, 30.32, 26.48, 26.02, 23.07, 10.89; Anal. Calcd for C$_{18}$H$_{26}$O$_2$: C, 78.79; H, 9.55; Found: C, 79.04, H, 9.41.

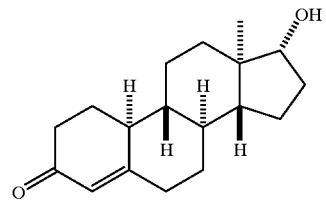

B. Preparation of (8α,9β,13α,14β,17α)-estra-1,3,5(10)-triene-3,17-diol,17acetate (ent-17β-estradiol,17-acetate).

Acetic anhydride (1.85 ml) was mixed with pyridine (5 ml) and stirred under nitrogen for 45 minutes and the ent-17β-nortestosterone (304 mg, 1.11 mmol) was added. The reaction vessel was purged with nitrogen and the reaction solution was stirred overnight. The following morning, 0.5 M HCl (15 ml) was added. After stirring for 1 hour, the reaction mixture was extracted with methylene chloride (3 portions of 30 ml). The combined organic extracts were washed with 1 N HCl (2 portions of 30 ml), saturated NaHCO$_3$ (1 portion of 30 ml) and brine (1 portion of 30 ml). The combined extracts were then dried with MgSO$_4$, filtered, and the solvents removed to give a yellow oil (0.37 g). Purification by chromatography (silica gel eluted with 20% ethyl acetate in hexanes) gave ent-19-nortestosterone,17-acetate as a colorless oil (0.32 g, 1.01 mmol, 91% yield) which was used in the next reaction. Ent-19-nortestosterone,17-acetate (0.32 g, 1.01 mmol) was dissolved in acetonitrile (10 ml). CuBr$_2$ (0.28 g, 1.25 mmol, 1.24 equivalents) was added. The reaction vessel was purged with nitrogen and the reaction was stirred overnight. The following morning, additional CuBr$_2$ (0.14 g, 0.63 mmol, 0.62 equivalents) was added. After an additional 2 hours, the reaction was quenched by the addition of water (15 ml). The acetonitrile was removed under reduced pressure. Additional water (10 ml) and brine (10 ml) were added. The reaction mixture was extracted with ethyl acetate (3 40 ml). The combined organic extracts were washed with brine (2 40 ml), dried with MgSO$_4$, filtered, and the solvents were removed to give a yellow solid (0.35 g). Purification by chromatography (silica gel, eluted with 20% ethyl acetate in hexanes) gave ent-17β-estradiol, 17-acetate (0.24 g, 0.76 mmol, 76% yield) as a white solid: mp 219–21° C.; IR 3419, 2927, 2871, 1708, 1611, 1585, 1546, 1500, 1447, 1375, 1358, 1274, 1181, 1153, 1132, 1039, 962 cm$^{-1}$; $^1$HNMR (300 MHz, CDCl$_3$) δ7.14 (1 H, d, J=8.4 Hz), 6.64–6.56 (2 H, m), 5.00 (1 H, s), 4.69 (1 H, dd, J=7.8 Hz, 9.3 Hz), 2.82 (2 H, m), 2.06 (3 H, s), 0.82 (3 H, s); $^{13}$C NMR (75 MHz, CDCl$_3$) δ171.59, 153.58, 138.27, 132.61, 126.60, 115.32, 112.77, 82.84, 49.73, 43.72, 42.85, 38.50, 36.83, 29.48, 27.47, 27.07, 26.12, 23.14, 21.08, 11.93.

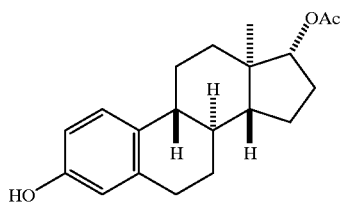

C. Preparation of (8α,9β,13α,14β,17α)-estra-1,3,5(10)-triene-3,17-diol (Ent-17β-estradiol).

The compound of (B), above, (0.21 g, 0.668 mmol) was dissolved in stirred EtOH (25 ml) and 10% aqueous NaOH (2.5 ml) was added. The reaction vessel was purged with nitrogen and the reaction was allowed to proceed overnight. The following morning, the reaction solution was quenched by the addition of 1N HCl (2 ml) and brine (50 ml). The reaction mixture was extracted with ethyl acetate (3 portions of 60 ml). The combined organic extracts were washed with brine (2 portions of 50 ml), filtered, and the solvents were removed to give a yellowish solid (0.20 g). Purification by chromatography gave ent-17β-estradiol as a white solid (174 mg, 0.64 mmol, 96%): mp 176–177° C.; [α]=−71.2 (c=0.99, CH$_3$OH); IR 3449, 3246, 2936, 2864, 1611, 1587, 1500, 1450, 1283, 1250, 1057, 1012, 930, 874 cm$^{-1}$; $^1$H NMR (300 MHz, CD$_3$OD) δ7.06 (1 H, d, J=8.7 Hz), 6.54–6.46 (2 H, m), 3.64 (1 H, t, J=8.4 Hz), 0.75 (3 H); $^{13}$C NMR (75 Hz, CD$_3$OD) δ156.07, 138.98, 132.80, 127.32, 116.18, 113.85, 82.57, 51.32, 45.34, 44.36, 40.50, 38.01, 30.67 (2 C), 28.48, 27.56, 23.99, 11.62.

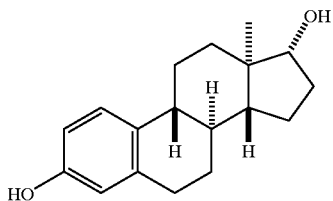

Example 7

Treatment of Stroke with Ent-17β-Estradiol

Sprague-Dawley female rats (20–225 grams body weight) were purchased from Charles River Laboratories, Inc. (Wilmington, Mass.). They were housed in pairs in hanging, stainless steel cage in a temperature controlled room (25° C.) with daily light cycle (light on 0700 to 1900 h daily) for a minimum of 3 days before surgery. All rats had free access to Purina Rat Chow and tap water. All procedures performed on animals were reviewed and approved by the Institutional Animal Care and Use Committee of the University of Florida before initiation of the study. Animals were ovariectomized at 1 week prior to middle cerebral artery (MCA) occlusion. At 2 hours prior to the MCA occlusion, animals received a subcutaneous injection of one of the following: corn oil vehicle (1 mg/kg body weight), 17β-estradiol (100 μg/kg body weight) or ent-17β-estradiol (100 μg/kg body weight).

MCAO was achieved according to the methods described previously by us. Briefly, following administration of anesthetics of ketamine (60 mg/kg, ip) and xylazine (10 mg/kg, ip), the common carotid artery (ICA) on the left side were exposed through a midline cervical incision and then gently dissected away from adjacent nerves. A 3-0 monofilament nylon suture was introduced into the left MCA lumen and gently advanced to the distal ICA until resistance was felt where the suture passed the bifurcation of the MCA and anterior cerebral artery (ACA). The thread was left in place for 60 minutes after which time re-perfusion was initiated. Rectal temperature was monitored and maintained between 36.5 and 37.0° C. during the entire stroke procedure. Each group of animals was decapitated after 24 hours of reperfusion. The brain was removed and placed in a metallic brain matrix for tissue slicing immediately after sacrifice. Five slices were made at 3, 4, 7, 9 and 11 m posterior to the olfactory bulb. The slices were incubated for 30 minutes in a 2% solution of 2,3,5-triphenyltetrazolium chloride (ITC) in physiological saline at 37° C. and then were fixed in 10% formalin. The stained slices were photographed and subsequently measured for the surface area of the slices and the ischemic lesion area. Ischemic lesion volume was calculated as by the sums of the areas of ischemic lesion across the five slices divided by the total cross sectional area of these five brain slices.

The results of pretreatment with 17β-estradiol or ent-17β-estradiol on the mean area for vehicle controls was 13.3±2.0 (mean±SEM). Treatment with 17β-estradiol reduced the infarct to 5.3±1.6, a reduction of 60%. Treatment with ent-17β-estradiol caused a similar decline in infarct area to 5.3±1.7. Dunn's Multiple Comparison test revealed that both the 17β-estradiol and the ent-17β-estradiol were significantly different from the vehicle control (p<0.05) but not from each other.

TABLE 1

Effects of Pretreatment with 17β-estradiol or an Estradiol Chemical Delivery System (E2-CDS) on Mortality Following Middle Cerebral Artery Occlusion.

| Treatment | Time of Planned Sacrifice | Number of Animals Tested | Number of Animals Alive | Number of Animals Dead | % Survival |
|---|---|---|---|---|---|
| Sham | 6 hrs | 12 | 5 | 7 | 42 |
| | 1 Day | 18 | 6 | 12 | 33 |
| | 1 Week | 5 | 1 | 4 | 20 |
| | Total | 35 | 12 | 23 | 35 |
| E2 Implant | 6 hrs | 6 | 3 | 3 | 50 |
| | 1 Day | 8 | 8 | 0 | 100* |
| | 1 Week | 4 | 3 | 1 | 75* |
| | Total | 18 | 14 | 4 | 78* |
| E2-CDS | 6 hrs | 7 | 5 | 2 | 71 |
| | 1 Day | 8 | 7 | 1 | 88* |
| | 1 Week | 4 | 4 | 0 | 100 |
| | Total | 19 | 16 | 3 | 84* |

*p < 0.05 versus sham control group at each of the time points, as determined by Chi Squares analysis.

TABLE 2

Effects of Estrogens on the Area Under the Ischemic Lesion Curve in Ovariectomized Rats.

| Steroid | Treatment | Area Under Curve |
|---|---|---|
| Sham | 24 hour pretreatment | 8.1 ± 0.8 |
| 17α-estradiol | 24 hour pretreatment | 3.7 ± 1.3* |
| HPCD Vehicle | 40 min post-treatment | 10.1 ± 1.6 |
| E2-CDS | 40 min post-treatment | 4.5 ± 0.9* |
| HPCD Vehicle | 90 min post-treatment | 8.2 ± 1.7 |
| E2-CDS | 90 min post-treatment | 5.21 ± 1.7 |

*p < 0.02 versus sham control by Students t test

TABLE 3

Diagram of the Synthesis of Ent-17-β-estradiol.

Scheme 1

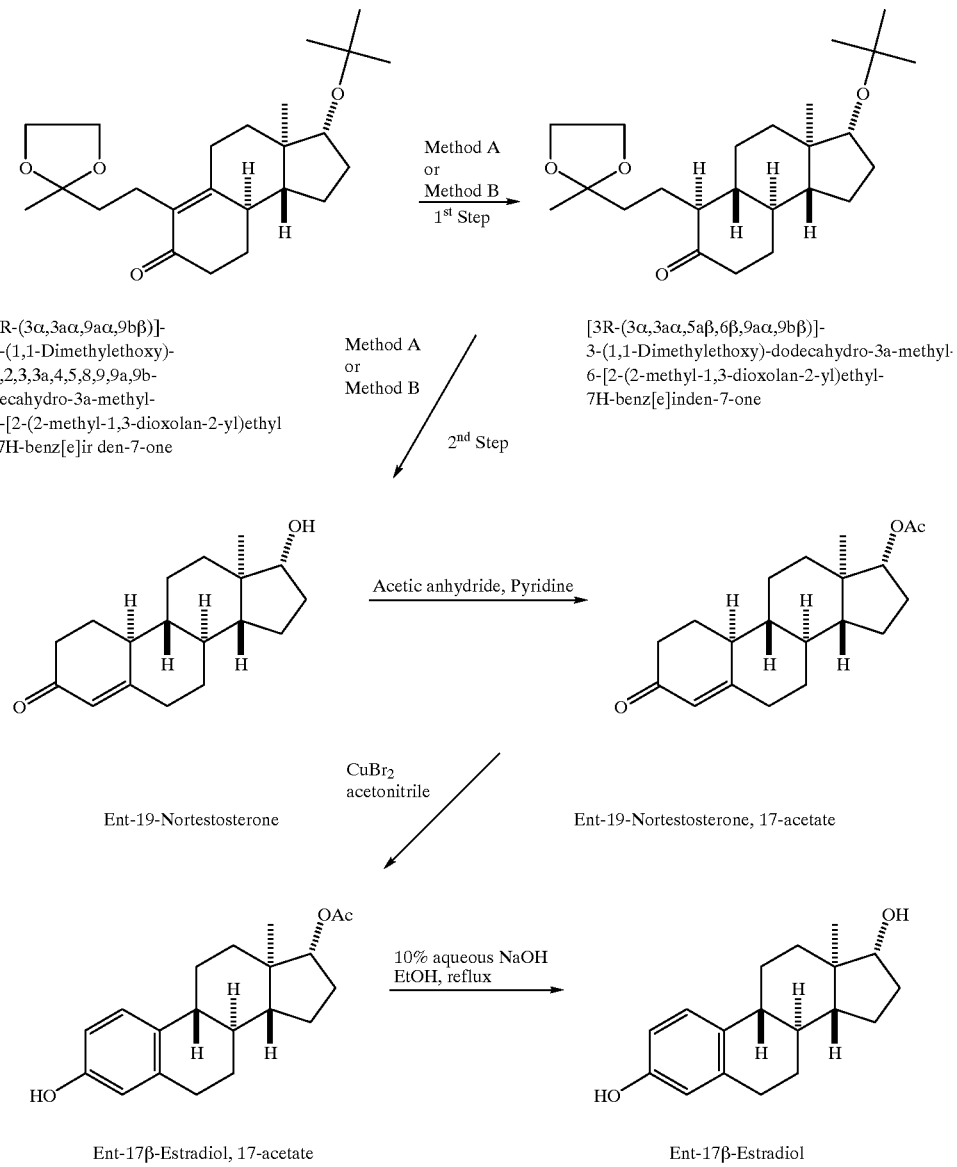

Reagents:
Method A, 1$^{st}$ Step, Li, liquid NH$_3$,THF; 2$^{nd}$ Step, 3N HCl, EtOH, reflux
Method B, 1$^{st}$ Step, H$_2$, Pd/C, EtOH; 2$^{nd}$ Step, 6N HCl, EtOH, reflux

We claim:

1. A method for conferring protection on a population of cells associated with ischemia in a subject, comprising:
   (a) providing ent-17β-estradiol; and
   (b) administering an effective amount of ent-17β-estradiol over a course that includes at least one dose within a time that is effectively proximate to the ischemic event so as to confer protection on the population of cells.

2. A method according to claim 1, wherein the proximate time precedes the ischemic event.

3. A method according to claim 1, wherein the proximate time follows the ischemic event.

4. A method according to claim 1, wherein the proximate time is within 12 hours of the ischemic event.

5. A method according to claim 1, wherein the ischemic event is selected from the group consisting of a cerebrovascular disease, stroke, subarachnoid hemorrhage, myocardial infarct, surgery and trauma.

6. A method according to claim 1, wherein the ischemic event is a stroke.

7. A method according to claim 1, wherein the ischemic event is a myocardial infarct.

8. A method according to claim 6, wherein the cells are neurons.

9. A method according to claim 6, wherein the cells are endothelial cells.

10. A method according to claim 6, wherein the cells are cardiac myocytes.

11. A method according to claim 1, wherein the estrogen compound is administered at an effective dose, wherein the effective dose provides a plasma concentration in the subject in the range of 10–500 pg/ml.

12. A method for conferring protection on a population of cells associated with ischemia, in a subject following an ischemic event, comprising:
   a) providing ent-17β-estradiol formulated in an oil vehicle; and
   b) administering an effective amount of the compound over a course that includes at least one dose within a time that is effectively proximate to the ischemic event, so as to confer protection on the population of cells.

13. A method according to claim 12, wherein the formulation is administered by a route selected from the group consisting of subcutaneous, transdermal and intravenous.

14. A method according to claim 12, wherein step (b) further comprises; administering the estrogen compound by subcutaneous injection.

15. A method according to claim 12, wherein step (b) further comprises; administering the estrogen compound intravenously.

16. A pharmaceutical formulation of an enantiomer of an estrogen compound, the formulation having insubstantial sex related activity, comprising: an effective amount of the enantiomer suitable for conferring protection on a population of cells in a subject.

17. A method for conferring protection on a population of cells, comprising:
   (a) providing ent-17β-estradiol; and
   (b) administering an effective amount of the ent-17β-estradiol so as to confer protection on the population of cells.

18. A method for protecting cells in a subject from degeneration during or after an ischemic event, comprising:
   (a) identifying a susceptible subject;
   (b) providing an effective dose of ent-17β-estradiol prior to the ischemic event; and
   (c) protecting cells from degeneration otherwise occurring in the absence of the ent-17β-estradiol.

19. A method of treating a myocardial infarct in a subject, comprising:
   (a) providing an effective dose of ent-17β-estradiol in a pharmaceutical formulation; and
   (b) administering the formulation to the subject so as to reduce the adverse effects of the myocardial infarct.

20. A method of treating an ischemic event in a subject, comprising:
   (a) providing ent-17β-estradiol; and
   (b) administering an effective cumulative amount of the enantiomer over a course that includes a first dose within a time that is effectively proximate to the ischemic event so as to confer protection on the population of cells.

21. A method of treating a neurodegenerative disorder in a subject, comprising:
   a) providing ent-17β-estradiol in a pharmaceutical formulation; and
   b) administering the formulation to the subject.

22. A composition, comprising ent-17β-estradiol, 17-acetate.

* * * * *